US008450374B2

(12) United States Patent
Koh et al.

(10) Patent No.: US 8,450,374 B2
(45) Date of Patent: *May 28, 2013

(54) PAN-ANTAGONISTS FOR THE ANDROGEN RECEPTOR AND ANDROGEN RECEPTOR MUTANTS ASSOCIATED WITH ANTI-ANDROGEN WITHDRAWAL

(75) Inventors: John Tze-tzun Koh, West Grove, PA (US); Paula Lynn McGinley, Langhorne, PA (US); Hongmu Pan, Newark, DE (US); Robert Sikes, Newark, DE (US)

(73) Assignee: University of Delaware, Newark, DE (US)

( * ) Notice: Subject to any disclaimer, the term of this patent is extended or adjusted under 35 U.S.C. 154(b) by 295 days.

This patent is subject to a terminal disclaimer.

(21) Appl. No.: 12/826,242

(22) Filed: Jun. 29, 2010

(65) Prior Publication Data
US 2010/0331418 A1 Dec. 30, 2010

Related U.S. Application Data

(60) Provisional application No. 61/221,318, filed on Jun. 29, 2009.

(51) Int. Cl.
*A61K 31/167* (2006.01)
*C07C 255/60* (2006.01)

(52) U.S. Cl.
USPC .......................... 514/618; 435/375; 558/393

(58) Field of Classification Search
USPC .......................... 514/618; 558/393; 435/375
See application file for complete search history.

(56) References Cited

U.S. PATENT DOCUMENTS

| | | | |
|---|---|---|---|
| 4,636,505 A | 1/1987 | Tucker | |
| 4,921,941 A | 5/1990 | Nagabhushan et al. | |
| 5,872,150 A | 2/1999 | Elbrecht et al. | |
| 6,071,957 A | 6/2000 | Miller et al. | |
| 6,593,492 B1 | 7/2003 | Ekwuribe et al. | |
| 6,812,362 B2 | 11/2004 | Ekwuribe et al. | |
| 7,022,869 B2 | 4/2006 | Ekwuribe | |
| 7,057,048 B2 | 6/2006 | Du et al. | |
| 7,550,505 B2 | 6/2009 | Koh et al. | |
| 7,807,713 B2 | 10/2010 | Koh et al. | |
| 2005/0137172 A1 | 6/2005 | Dalton et al. | |
| 2005/0209320 A1 | 9/2005 | Miller et al. | |
| 2009/0156614 A1 | 6/2009 | Dalton et al. | |
| 2010/0016279 A1 | 1/2010 | Bradbury et al. | |

FOREIGN PATENT DOCUMENTS
WO    WO 2008/013791 A2    1/2008

OTHER PUBLICATIONS

Hara, T., et al., "Novel mutations of androgen receptor: A possible mechanism of bicalutamide withdrawal syndrome", Cancer Res., vol. 63, pp. 149-153 (2003).
Hara, T., et al., "Possible role of adaptive mutation in resistance to antiandrogen in prostate cancer cells", Prostate, vol. 65, pp. 268-275 (2005).
Hara, T., et al., "Androgen receptor and invasion in prostate cancer", Cancer Res., vol. 68, pp. 1128-1135 (2008).
Notice of Allowability in U.S. Appl. No. 12/466,805, mailed Jun. 21, 2010.
Non-Final Office Action in U.S. Appl. No. 11/880,725, mailed Aug. 13, 2008.
Final Office Action in U.S. Appl. No. 11/880,725, mailed Feb. 18, 2009.
Notice of Allowability in U.S. Appl. No. 11/880,725, mailed Mar. 23, 2009.
Amselem, S. et al., "In Vitro Tests to Predict In Vivo Performance . . . ", Chemistry and Physics of Lipids, vol. 64, pp. 219-237 (1993).
Burnham, NL, "Polymers for Delivering Peptides and Proteins", Amer. J. Health-System Pharmacy, vol. 51, pp. 210-218 (1994).
Chen, B. et al., "Nucleophilic Aromatic Substituion of Methacrylamide Anion . . . ", J. Org. Chem., vol. 68, pp. 10181-10182 (2003).
Davis, FF et al., "Enzyme-Polyethylene Glycol Adducts . . . ", Enzyme Engineering, vol. 4, pp. 169-173 (1978).
Friden, PM et al., "Blood-Brain Barrier Penetration and In Vivo Activity of an NGF . . . ", Science, vol. 259, pp. 373-377 (1993).
McGinley, P., et al, "Circumventing anti-androgen resistance by molecular design", J. Am. Chem. Soc., vol. 129, pp. 3822-3823 (2007).
Murata, M. et al., "A General and Efficient Method for the Palladium-Catalyzed, . . . ", Tetrahedron, vol. 60, pp. 7397-7403 (2004).
Tucker, H. et al., "Nonsteroidal Antiandrogens, Synthesis and Structure . . . ", J. Med. Chem., vol. 31, pp. 954-959 (1998).
Zheng, N. et al., "Palladium-Catalyzed Synthesis of Aryl Sulfides . . . ", J. Org. Chem., vol. 63, pp. 9606-9607 (1998).
International Search Report and Written Opinion in International Application No. PCT/US2010/040391, mailed Feb. 22, 2011.

*Primary Examiner* — Sreeni Padmanabhan
*Assistant Examiner* — Uma Ramachandran
(74) *Attorney, Agent, or Firm* — Potter Anderson & Corroon LLP

(57) ABSTRACT

Disclosed herein are novel antagonists of the androgen receptor and androgen receptor mutations associated with clinical failure of currently prescribed anti-androgens and use of said antagonists in the treatment of conditions associated with inappropriate activation of the androgen receptor.

4 Claims, 18 Drawing Sheets

PAN 52

PAN52 Day 5

PAN52 Day 5

Control Day 5

PAN52 Day 3

Control Day 3

PAN-ANTAGONISTS FOR THE ANDROGEN RECEPTOR AND ANDROGEN RECEPTOR MUTANTS ASSOCIATED WITH ANTI-ANDROGEN WITHDRAWAL

CROSS-REFERENCE

This application claims priority from U.S. Provisional Application Ser. No. 61/221,318 filed Jun. 29, 2009, which is incorporated by reference herein in its entirety.

GOVERNMENT INTERESTS

This invention was made with government support under Grant No. R01 DK054257-08A1 awarded by the National Institutes of Health. The government has certain rights in this invention.

FIELD OF THE INVENTION

Disclosed herein are novel antagonists of the androgen receptor and mutant forms of the androgen receptor associated with clinical failure of currently prescribed anti-androgens.

BACKGROUND OF THE INVENTION

Thirty to forty percent of prostate cancer patients become androgen independent (resistant to anti-androgen treatment) within five years of anti-androgen therapy. In many instances, cancer cells adapt by changing receptor or cofactor expression levels, or acquire androgen receptor mutations that cause anti-androgens to act as agonists or to change receptor specificity. In these cases, alternative treatment regimes are needed. Exemplary treatments can be found in U.S. Pat. No. 4,636,505, which discloses acylanilides that have anti-androgenic properties, and U.S. Pat. No. 7,057,048, which discloses 6-sulfonamido-quinolin-2-one and 6-sulfonamido-2-oxo-chromeme derivatives and their use as androgen antagonists.

Androgen receptor mutations are found in as many as 50% of metastatic, hormone refractory prostate cancer tumors. Studies suggest that 12-24% of hormone refractory metastases from patients treated with flutamide contain the same T877A mutation which causes flutamide to act as an agonist instead of an antagonist. Mutations such as AR(W741 C) have emerged in response to second generation antiandrogens such as bicalutamide and can similarly lead to clinical failure. Anti-androgen resistance also can be caused by abnormal androgen signaling often associated with anomalous expression or modification of androgen receptor or receptor cofactors. Resistance to some antiandrogens has also been associated with androgen receptor overexpression. Residual receptor activity in the presence of antagonists has been observed with other nuclear receptors and in some cases has been effectively blocked by appropriate antagonists bearing long polar extensions that are believed to more effectively block co-factor recruitment and alter or block receptor functions essential for specific cellular activities. By analogy, antiandrogens with long polar extensions similarly would be expected to have a superior ability to block residual androgen signaling and reduce and/or delay the occurrence of anti-androgen resistance.

SUMMARY OF THE INVENTION

One aspect relates to a compound of the formula:

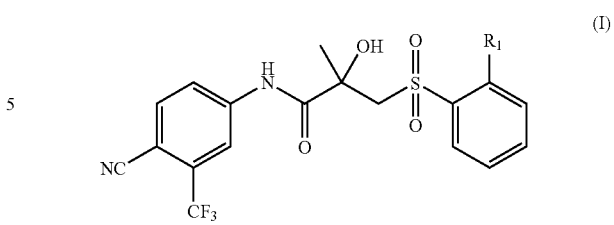

wherein $R_1$ is phenyl phenoxy, benzoyl, phenylthio or benzyl, said $R_1$ being substituted with alkyl, branched alkyl, alkoxy, branched alkoxy, aryl, aryloxy, alkylamido, alkylcarbamoyl, or acyl; said substituted groups being further optionally substituted with alkyl, amino, alkylamino, dialkylamino, arylamino, acyl, ester, carboxyl, hydroxyl, alkoxy, sulfonyl or cyano.

A further aspect is for a method for the treatment of a mammal suffering from an androgen-dependent disorder comprising administering to the mammal in need thereof a therapeutically effective amount of a compound of Formula (I).

An additional aspect relates to a method for the treatment of a mammal suffering from an androgen-dependent disorder comprising administering to the mammal in need thereof a therapeutically effective amount of a compound of Formula (II), (III), (IV), (V), (VI), (VII), (VIII), (IX), (X), or a combination thereof.

An additional aspect if for a method for the treatment of a mammal suffering from benign prostatic hyperplasia comprising administering to the mammal in need thereof a therapeutically effective amount of a compound of Formula (II), (III), (IV), (V), (VI), (VII), (VIII), (IX), (X), or a combination thereof.

A further aspect is for a method for monitoring the effectiveness of treatment of a subject with a compound of Formula (I) comprising the steps of (i) obtaining a pre-administration sample from a subject prior to administration of the compound; (ii) detecting the level of androgen receptor activity in the pre-administration sample; (iii) obtaining one or more post-administration samples from the subject; (iv) detecting the level of androgen receptor activity in the post-administration samples; comparing the level of androgen receptor activity in the pre-administration sample with the post administration sample or samples; and altering the administration of the compound to the subject accordingly.

Another aspect is for a method for monitoring the effectiveness of treatment of a subject with a compound of Formula (II), (III), (IV), (V), (VI), (VII), (VIII), (IX), (X), or a combination thereof comprising the steps of (i) obtaining a pre-administration sample from a subject prior to administration of the compound; (ii) detecting the level of androgen receptor activity in the pre-administration sample; (iii) obtaining one or more post-administration samples from the subject; (iv) detecting the level of androgen receptor activity in the post-administration samples; (v) comparing the level of androgen receptor activity in the pre-administration sample with the post administration sample or samples; and (vi) altering the administration of the compound to the subject accordingly.

A further aspect is for a method of reducing androgen receptor overexpression comprising contacting a cell comprising overexpressed androgen receptor with a compound of the Formula (II), (III), (IV), (V), (VI), (VII), (VIII), (IX), (X), or a combination thereof thereby decreasing androgen receptor expression in the cell.

Other objects and advantages will become apparent to those skilled in the art upon reference to the detailed description that hereinafter follows.

DETAILED DESCRIPTION OF THE INVENTION

Figure 1:
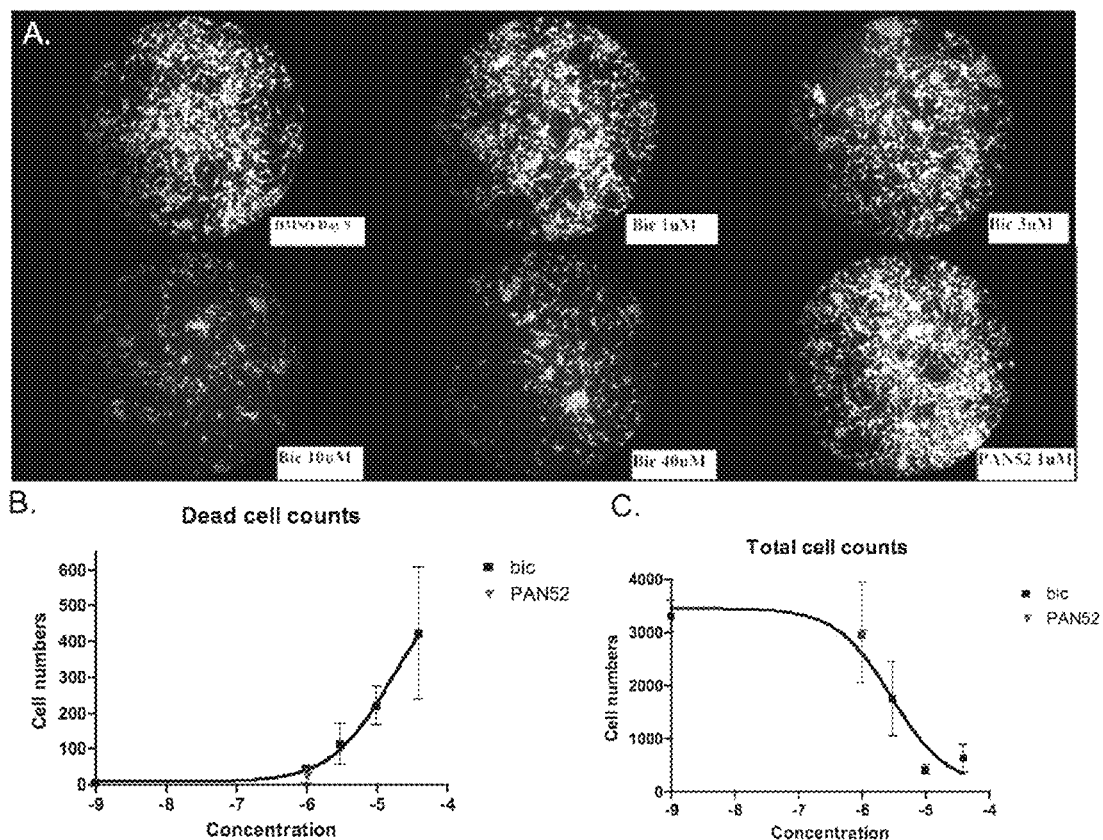
FIG. 1. LnCaP cell LIVE/DEAD toxicity assay with PAN52 (Formula IX) and Bicalutamide. A. Fluorescence images showing viable (green: almost all cells in DMSO Day 9, Bic 1 µM, and PAN52 1 µM panels; majority of cells in Bic 3 µM panel) and dead cells (red: some cells in Bic 3 µM panel, and almost all cells in Bic 10 µM and Bic 40 µM panels). The pictures were taken after nine days of incubation in RPMI supplemented with 10% DCC-FBS plus indicated antiandrogens. B and C. Quantitative analysis of images.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Disclosed herein are bicalutamide analogs that more fully block co-activator and other cofactor recruitment to the androgen receptor based on structural models. These are the first examples of bicalutamide analogs to contain polar molecular extensions expected to access the receptor surface and retain potencies similar to bicalutamide. Further, the compounds are structurally incompatible with molecular mechanisms that cause antagonists such as bicalutamide to become agonists in AR mutants.

Herein, Applicants show that these compounds resist formation of resistant LNCaP clones in in vitro cell based assays. The ability to evade resistance is believed to be not due to the compounds toxicity but rather the result of their molecular mode of inactivating cellular AR. LNCaP cells have been shown to recapitulate aspects of antiandrogen resistance observed in vivo, including changes in AR expression, cell invasiveness and selection of AR mutations associated with promiscuous and or antiandrogen withdrawal syndrome (Cancer Research 2008, 68, 1128-1135; Cancer Research 2003, 63149-153; The Prostate 2005, 65, 268-275). These assays are therefore not biased towards any one mechanism of resistance. Compounds that evade antiandrogen resistance in these in vivo models are reasonably expected to have properties that impart a superior ability to evade antiandrogen resistance in vivo.

I. DEFINITIONS

In the context of this disclosure, a number of terms shall be utilized.

The term "androgen" includes all known compounds with androgenic activity. Androgenic activity of compounds may be determined in a variety of ways including in cell-based AR transcription assays and in biological activity assays where a compound can be demonstrated to have activity that is similar to the activity of known androgens. These assays can be performed using animals or tissues. For example, compounds with androgen activity in the prostate are able to stimulate prostate growth in rodents. Natural androgen metabolites that have biological activity can be used and include, for example, testosterone, androstenedione, androstanedione, and dihydrotestosterone (DHT).

The term "androgen-dependent disorder" refers to any disorder that can benefit from a decrease in androgen stimulation and includes pathological conditions that depend on androgen stimulation. An "androgen-dependent disorder" can result from an excessive accumulation of testosterone or other androgenic hormone, increased sensitivity of androgen receptors to androgen, an increase in androgen-stimulated transcription or benefit from a decrease in androgen response. Examples of "androgen-dependent disorders" include prostate cancer, refractory prostate cancer and skin disorders such as, for example, acne, seborrhea, hirsutism, alopecia, or hidradenitis suppurativa.

The term "androgen receptor" or "AR" refers to the androgen receptor protein as defined by its conserved amino acid coding sequence in an active or native structural conformation. Nucleic acid sequences encoding androgen receptors have been cloned and sequenced from numerous organisms. Representative organisms and GenBank® accession numbers for androgen receptor sequences therefrom include the following: frog (*Xenopus laevis*, NM_001090884.1), mouse (*Mus musculus*, NM_013476.1), rat (*Rattus norvegicus*, NM_012502.1), human (*Homo sapiens*, NM_000044.2), canine (*Canis familiaris*, NM_001003053.1), rhesus monkey (*Macaca mulatta*, NM_001032911.1), zebrafish (*Danio rerio*, NM_001083123.1), chimpanzee (*Pan troglodytes*, NM_001009012.1), chicken (*Gallus gallus*, NM_001040090.1), pig (*Sus scrofa*, NM_214314.1), horse (*Equus caballus*, NM_001163891.1), rabbit (*Oryctolagus cuniculus*, U16366.1), cow (*Bos taurus*, Z75313.1, Z75314.1, Z75315.1), canary (*Serinus canaria*, L25901.1), and whiptail lizard (*Cnemidophous uniparens*, S79938.1).

The term "androgen receptor overexpression" or "AR overexpression" means the state of cells or tissues having abnormally high concentrations of the androgen receptor. This can be caused by several mechanisms including increased transcription of the genes encoding AR, increased translational activity of AR, and/or increased cellular stability of AR. AR overexpression is known to cause cells to become resistant to antiandrogens in current clinical use. Some antiandrogens can also modulate expression of cytokines which can enhance a survival response to prostatic tissues.

The term "anti-androgen" as used herein refers compounds that specifically block the actions of androgens on the AR. Anti-androgens are believed to act by competitively inhibiting the action of androgens by binding to androgen receptors and/or mutant forms of the androgen receptor, and preventing androgens from binding to the receptors and entering the cell nucleus. Formula I compounds are examples of anti-androgens.

Anti-androgen resistance refers to the state of a androgen dependent tissue or cell which no longer responds to a specific anti-androgens in a specific androgen responsive assay.

The term "benign prostatic hyperplasia" or "BPH" refers to a benign adenoma derived from a transitional region of the prostate, in which prostate epithelial cells grow abnormally and block urine flow.

The terms "effective amount", "therapeutically effective amount", and "effective dosage" as used herein, refer to the amount of a Formula I compound that, when administered to a mammal in need, is effective to at least partially ameliorate a condition from which the mammal is suspected to suffer.

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal. The skilled person also appreciates that credible animal models of human prostate cancer pathologies are known.

II. ANTI-ANDROGEN COMPOUNDS

One aspect is for a compound of the formula:

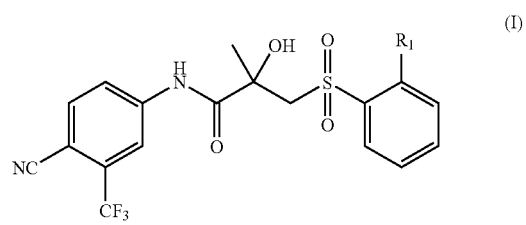

(I)

wherein $R_1$ is phenyl phenoxy, benzoyl, phenylthio or benzyl, said $R_1$ being substituted with alkyl, branched alkyl, alkoxy, branched alkoxy, aryl, aryloxy, alkylamido, or acyl; said substituted groups being further optionally substituted with alkyl, amino, alkylamino, dialkylamino, arylamino, acyl, ester, carboxyl, hydroxyl, alkoxy, sulfonyl or cyano.

In another embodiment, the compound can be selected from the group consisting of:

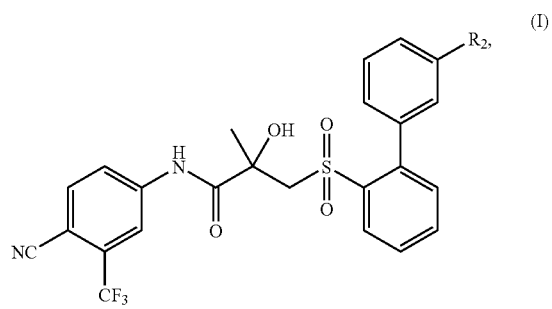

(I)

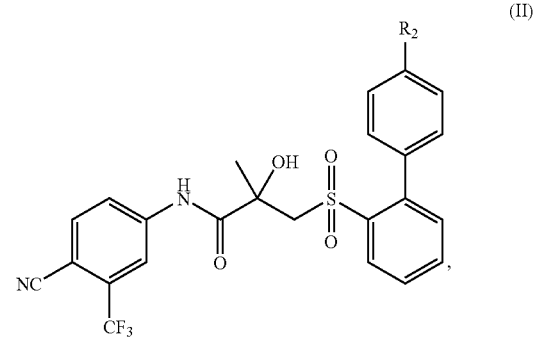

(II)

-continued (III)
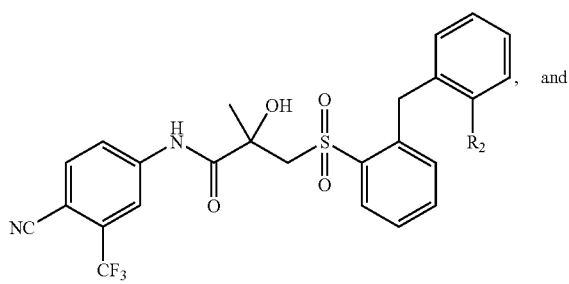

(IV)
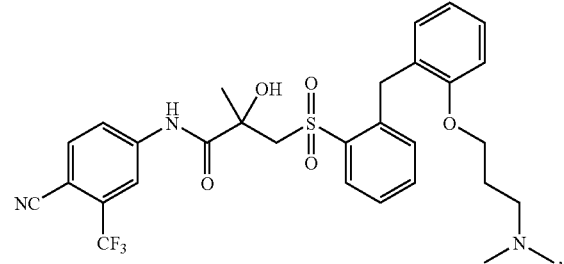

wherein R₂ is alkyl, alkoxy, aryl, branched alkyl, branched alkyloxy, alkylamino, dialkylamino, aryloxy, arylamino, acyl, alkylamido, or alkylcarbamoyl, said R₂ group optionally being substituted with alkyl, amino, alkylamino, dialkylamino, carboxyl, ester, hydroxy, alkoxy, sulfonyl or cyano.

Formula I compounds of particular interest include, for example, (V)
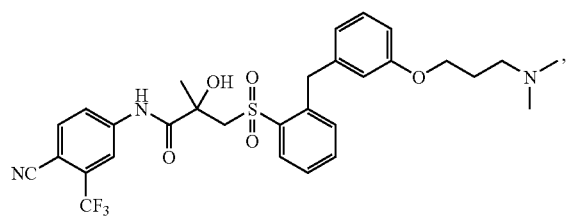

(VI)

-continued (VII)
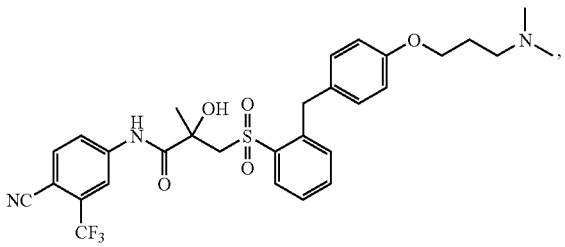

(VIII)
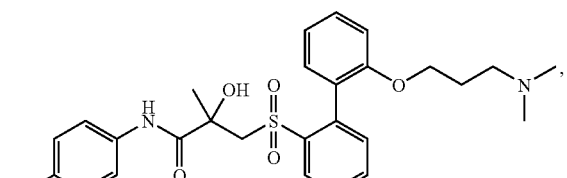

(IX)
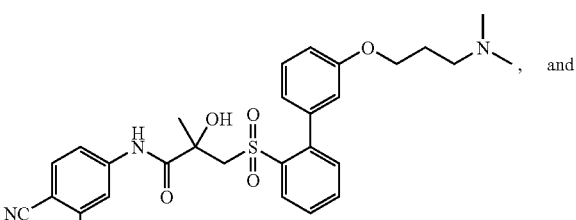

(X)
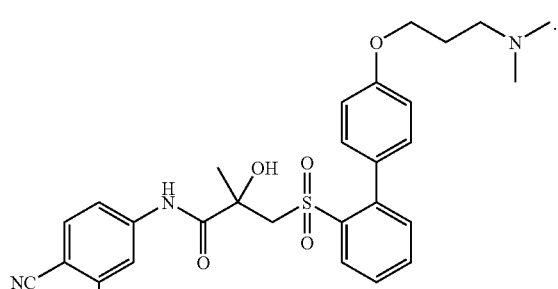

III. GENERAL FORMULA I COMPOUND SYNTHETIC SCHEME

Thiols were synthesized from their corresponding anilines or amines, when not commercially available. Briefly, concentrated hydrochloric acid was added to a cooled solution of amine or aniline dissolved in water. A cooled solution of sodium nitrite in water was added slowly and the reaction stirred for 30 minutes. This solution was then added to a solution of potassium ethyl xanthate in water warmed to 45° C. and stirred for a further 30 minutes. Diethyl ether was added and the organic layer was washed with 10% sodium hydroxide and water until neutral. The organic layer was dried over magnesium sulfate, filtered and evaporated. The crude product was then dissolved in ethanol and heated to reflux. Potassium hydroxide pellets were added and refluxing was continued overnight. The ethanol was evaporated. The residue was diluted with water and extracted with diethyl ether. The aqueous layer was acidified with 2 N HCl and extracted with diethyl ether. The organic layer was separated, dried over magnesium sulfate, filtered and evaporated to yield the crude thiol, which could be further purified by column chromatography if necessary. Alternatively, thiols can be generated by transition metal mediated cross coupling with aryl halides or aryl triflates (see, for example: Buchwald et al., Tetrahedron, 2004, 60, 7397, and Zheng et al., J. Organic Chemistry, 1998, 63, 9606).

Aryl and alkyl amines can be derived directly from their corresponding nitro compounds. Briefly, the nitro compound and 10% palladium on carbon were dissolved in methanol and purged with nitrogen then placed under an atmosphere of hydrogen overnight or until the reaction was complete. The reaction mixture was filtered and solvent evaporated to yield the desired amine.

The thiols were added to the epoxide, N-(4-Cyano-3-trifluorophenyl)methacrylamide epoxide, to form the sulfide intermediate. This epoxide was synthesized following published procedures. (For example: Chen et al., J. Organic Chemistry, 2003, 68, 10181 and Tucker, H., Crook, J. W. and Chesterson, J. W., J. Med. Chem. 1988, 31, 954.)

The epoxide ring opening was achieved using a base and the appropriate thiol in a suitable solvent. For example, sodium hydride (60% dispersed in mineral oil) was suspended in THF (tetrahydrofuran) and cooled to 0° C. A solution of the thiol in THF was added via syringe and stirred for 5 minutes. N-(4-Cyano-3-trifluorophenyl)methacrylamide epoxide dissolved in THF was added slowly. The reaction was allowed to warm to room temperature and stirred overnight. The solvent was evaporated. The residue was diluted with water and extracted with ethyl acetate. The organic layer was washed with water and brine, dried over magnesium sulfate, filtered and evaporated. The compound was purified by column chromatography.

The sulfide intermediate was oxidized to give the final desired sulfone compounds. Briefly, the sulfide was dissolved in dichloromethane and cooled to −78° C. 30% hydrogen peroxide was added followed by the slow addition of trifluoroacetic anhydride. The reaction was stirred at room temperature for 16 h. The reaction was diluted with dichloromethane and cold water and brine were added. The reaction was stirred for 20 minutes. The organic layer was separated, dried over magnesium sulfate, filtered and evaporated. The compound was purified by column chromatography.

Some of the compounds of Formula I will exist as optical isomers. Any reference in this application to one of the compounds represented by Formula I is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively, utilization of a specific optical isomer as the starting material will produce the corresponding isomer as the final product.

IV. ADMINISTRATION OF ANTI-ANDROGENS

Formula I compounds can be administered to subjects in a biologically compatible form suitable for pharmaceutical administration in vivo. By "biologically compatible form suitable for administration in vivo" is meant a form of the Formula I compound to be administered in which any toxic effects are outweighed by the therapeutic effects of the compound. The term subject is intended to include living organisms in which an immune response can be elicited, for example, mammals. Administration of a Formula I compound as described herein can be in any pharmacological form including a therapeutically active amount of a Formula I compound alone or in combination with a pharmaceutically acceptable carrier.

A therapeutically effective amount of a Formula I compound may vary according to factors such as the disease state, age, sex, and weight of the individual, and the ability of the compound to elicit a desired response in the individual. Dosage regime may be adjusted to provide the optimum therapeutic response. For example, several divided doses may be administered daily, or the dose may be proportionally reduced as indicated by the exigencies of the therapeutic situation.

The therapeutic or pharmaceutical compositions can be administered by any suitable route known in the art including, for example, intravenous, subcutaneous, intramuscular, transdermal, intrathecal, or intracerebral or administration to cells in ex vivo treatment protocols. Administration can be either rapid as by injection or over a period of time as by slow infusion or administration of slow release formulation. For treating prostate cancer, administration of the therapeutic or pharmaceutical compositions of the present invention can be performed, for example, orally or subcutaneously. For skin disorders, administration of the therapeutic or pharmaceutical compositions of the present invention can be performed, for example, topical or oral administration.

Formula I compounds can also be linked or conjugated with agents that provide desirable pharmaceutical or pharmacodynamic properties. For example, Formula I compounds can be coupled to any substance known in the art to promote penetration or transport across the blood-brain barrier such as an antibody to the transferrin receptor, and administered by intravenous injection (see, e.g., Friden P M et al., Science 259:373-77 (1993)). Furthermore, Formula I compounds can be stably linked to a polymer such as polyethylene glycol to obtain desirable properties of solubility, stability, half-life, and other pharmaceutically advantageous properties (see, e.g., Davis et al., Enzyme Eng. 4:169-73 (1978); Burnham N L, Am. J. Hosp. Pharm. 51:210-18 (1994)).

Furthermore, Formula I compounds can be in a composition which aids in delivery into the cytosol of a cell. For example, a Formula I compound may be conjugated with a carrier moiety such as a liposome that is capable of delivering the compound into the cytosol of a cell. Such methods are well known in the art (see, e.g., Amselem S et al., Chem. Phys. Lipids 64:219-37 (1993)). Alternatively, the compound can be delivered directly into a cell by microinjection.

The Formula I compounds are usefully employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. Formula I compounds can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Formula I compounds may be used individually or in combination and with other anti-androgens or other treatments, such as flutamide, bicalutamide, and nilutamide; irradiation; heat; luteinizing hormone-releasing hormone or luteinizing hormone-releasing hormone analog, such as goserelin; or the like, as may be conventionally employed and as may be moderated for use in conjunction with the Formula I compounds.

Dose administration can be repeated depending upon the pharmacokinetic parameters of the dosage formulation and the route of administration used.

It is also provided that certain formulations containing the Formula I compounds are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents, or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

In some embodiments, Formula I compounds are utilized for the treatment of androgen-related diseases of the skin such as, for example, acne, seborrhea, hirsutism, alopecia, or hidradenitis suppurativa. When used for any of these purposes, the Formula I compounds are preferably administered topically together with a conventional topical carrier or diluent. When used topically, it is preferred that the diluent or carrier does not promote transdermal penetration of the active ingredients into the blood stream or other tissues where they might cause unwanted systemic effects.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the anti-androgen activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such compounds can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment, the present invention provides a method for monitoring the effectiveness of treatment of a subject with a Formula I compound comprising the steps of (i) obtaining a pre-administration sample from a subject prior to administration of the compound; (ii) detecting the level of androgen receptor activity in the pre-administration sample; (iii) obtaining one or more post-administration samples from the subject; (iv) detecting the level of androgen receptor activity in the post-administration samples; (v) comparing the level of androgen receptor activity in the pre-administration sample with the post administration sample or samples; and (vi) altering the administration of the compound to the subject accordingly. For example, increased administration of the Formula I compound may be desirable to decrease the activity of androgen receptor to lower levels than detected, that is, to increase the effectiveness of the compound. Alternatively, decreased administration of the compound may be desirable to increase androgen receptor activity to higher levels than detected, that is, to decrease the effectiveness of the compound.

In another embodiment, the ability of a Formula I compound to modulate androgen receptor activity in a subject that would benefit from modulation of the activity of the androgen receptor can be measured by detecting an improvement in the condition of the patient after the administration of the compound. Such improvement can be readily measured by one of ordinary skill in the art using indicators appropriate for the specific condition of the patient. Monitoring the response of the patient by measuring changes in the condition of the patient is preferred in situations where the collection of biopsy materials would pose an increased risk and/or detriment to the patient.

Furthermore, in the treatment of disease conditions, compositions containing Formula I compounds can be administered exogenously and it would likely be desirable to achieve certain target levels of Formula I compounds in sera, in any desired tissue compartment, or in the affected tissue. It would, therefore, be advantageous to be able to monitor the levels of Formula I compounds in a patient or in a biological sample including a tissue biopsy sample obtained from a patient. Accordingly, the present invention also provides methods for detecting the presence of Formula I compounds in a sample from a patient.

Some embodiments are directed to the reduction of androgen receptor overexpression. Compounds of Formula I can be used to contact a cell comprising overexpressed androgen receptor thereby decreasing androgen receptor expression. Methods of administering anti-androgens, as described in this section, are useful for contacting cells with the Formula I compounds.

In a preferred embodiment, the cells components of or originate from the prostate epithelium and/or the prostate stroma.

In addition to Formula I compounds, compounds from Published U.S. Patent Application No. 2008/0064757 can also be useful in reducing androgen receptor overexpression. These compounds have the formula

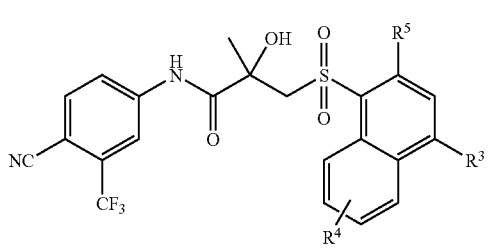
(XI)

wherein $R^3$ is hydrogen, fluorine, chlorine, bromine, cyano, hydroxy, methyl acrylate, or $C_1$-$C_6$ alkyl optionally substituted with hydroxy;
$R^4$ is hydrogen, hydroxy, fluoro, chloro, cyano, $C_1$-$C_5$ alkanoate, $C_1$-$C_5$ alkylamino, or $C_1$-$C_6$ alkyl optionally substituted with hydroxy or acrylate; and
$R^5$ is hydrogen, $C_1$-$C_6$ alkyl, fluoro, chloro, bromo, or cyano; or have the formula

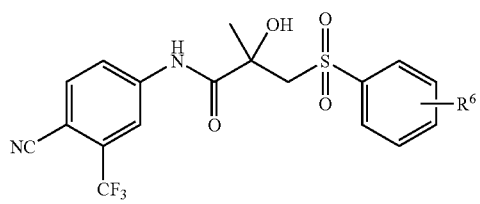
(XI)

wherein $R^6$ is phenyl optionally substituted with hydroxy; $C_1$-$C_6$ phenylalkyl; or benzyl optionally substituted with hydroxy, $C_1$-$C_6$ alkoxy optionally substituted with methoxy or cyano, $C_1$-$C_6$ alkyl, $C_1$-$C_5$ alkanoate, or $C_1$-$C_5$ alkylamine. Preferred compounds of Formulas X and XI include, e.g.,

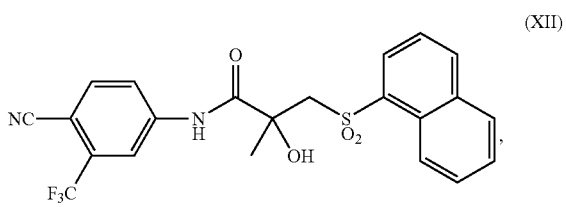
(XII)

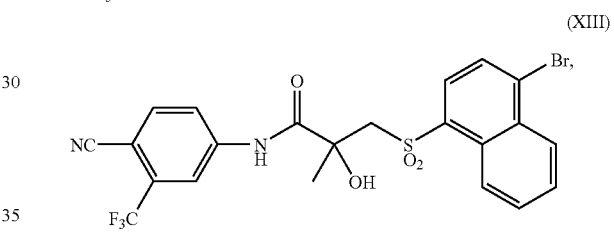
(XIII)

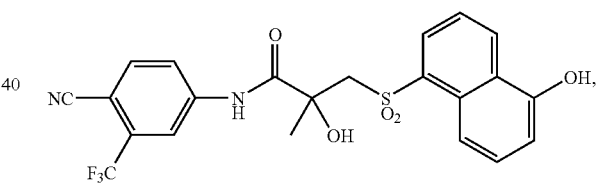
(XIV)

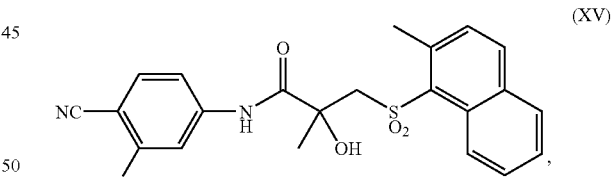
(XV)

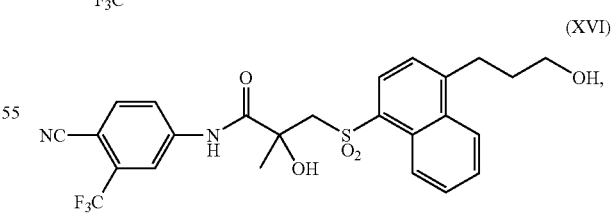
(XVI)

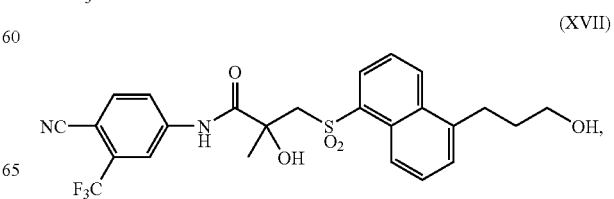
(XVII)

(XVIII)
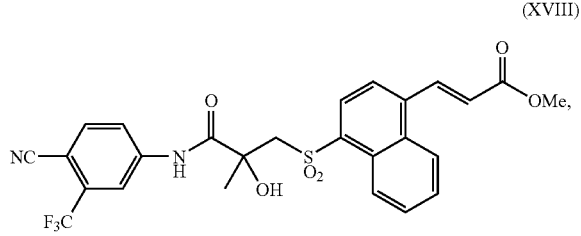
(XIX)
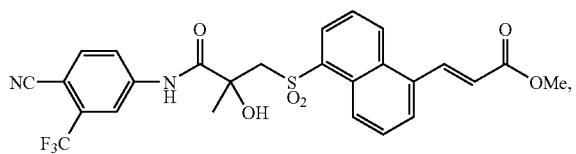
(XX)
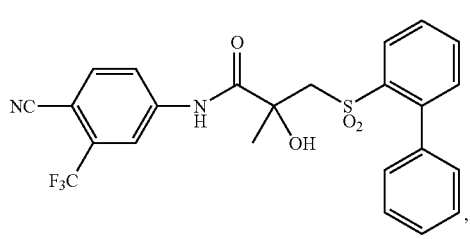
(XXI)
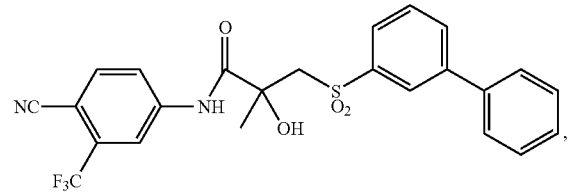
(XXII)
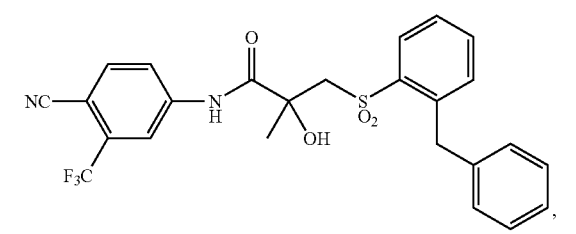
(XXIII)
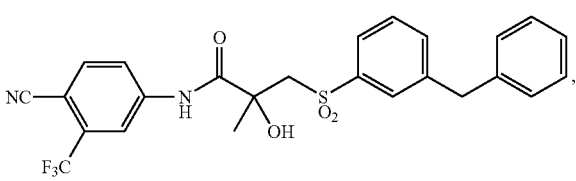
(XXIV)
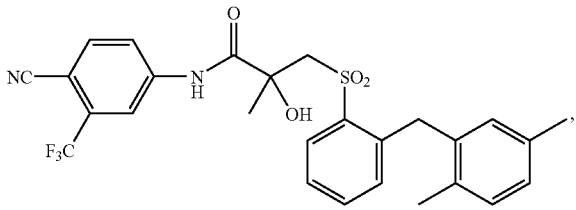
(XXV)
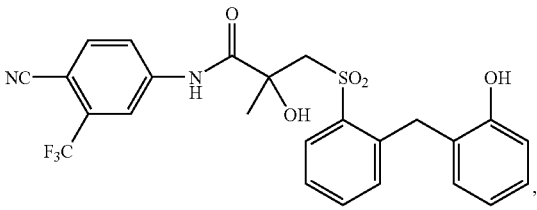
(XXVI)
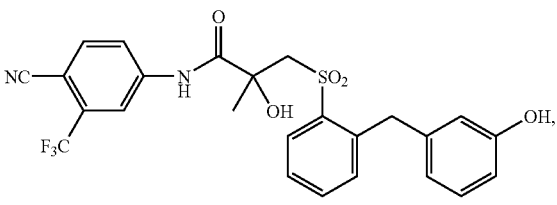
(XXVII)
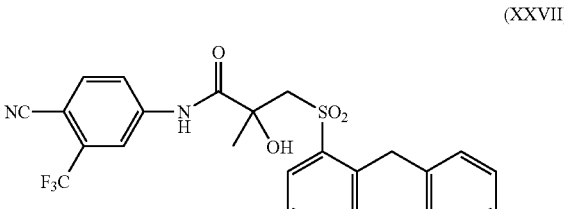
(XXVIII)
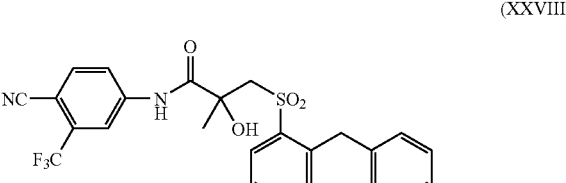
(XXIX)
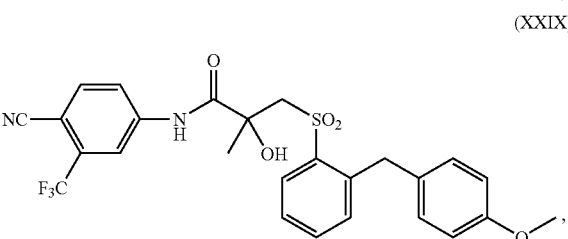
(XXX)
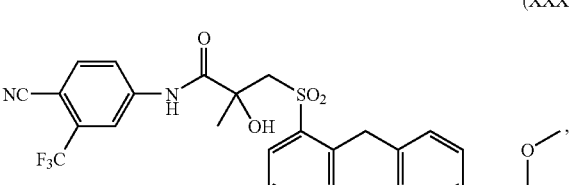
(XXXI)
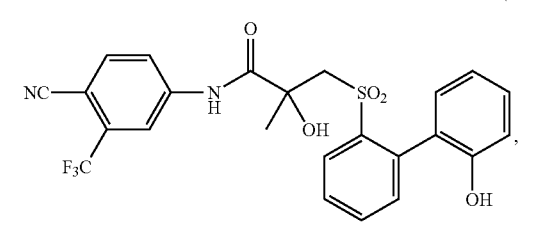

-continued

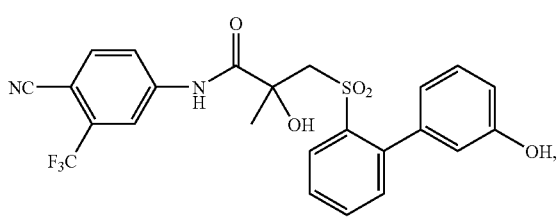

(XXXII)

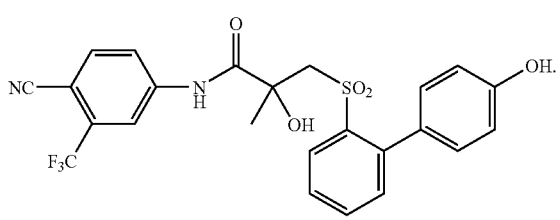

(XXXIII)

All of the compositions and methods disclosed and claimed herein can be made and executed without undue experimentation in light of the present disclosure. It will be apparent to those of skill in the art that variations may be applied to the compositions and methods and in the steps or in the sequence of steps of the method described herein without departing from the concept, spirit, and scope of the invention. More specifically, it will be apparent that certain agents which are chemically or biologically related may be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples are given by way of illustration only. From the above discussion and these Examples, one skilled in the art can ascertain the preferred features of this invention, and without departing from the spirit and scope thereof, can make various changes and modifications of the invention to adapt it to various uses and conditions.

Example 1

N-(4-cyano-3-(trifluoromethyl)phenyl)-3-(2'-(3-(dimethylamino)propoxy)biphenyl-2-ylsulfonyl)-2-hydroxy-2-methylpropanamide PAN42 (Formula XIII)

Figure 10:
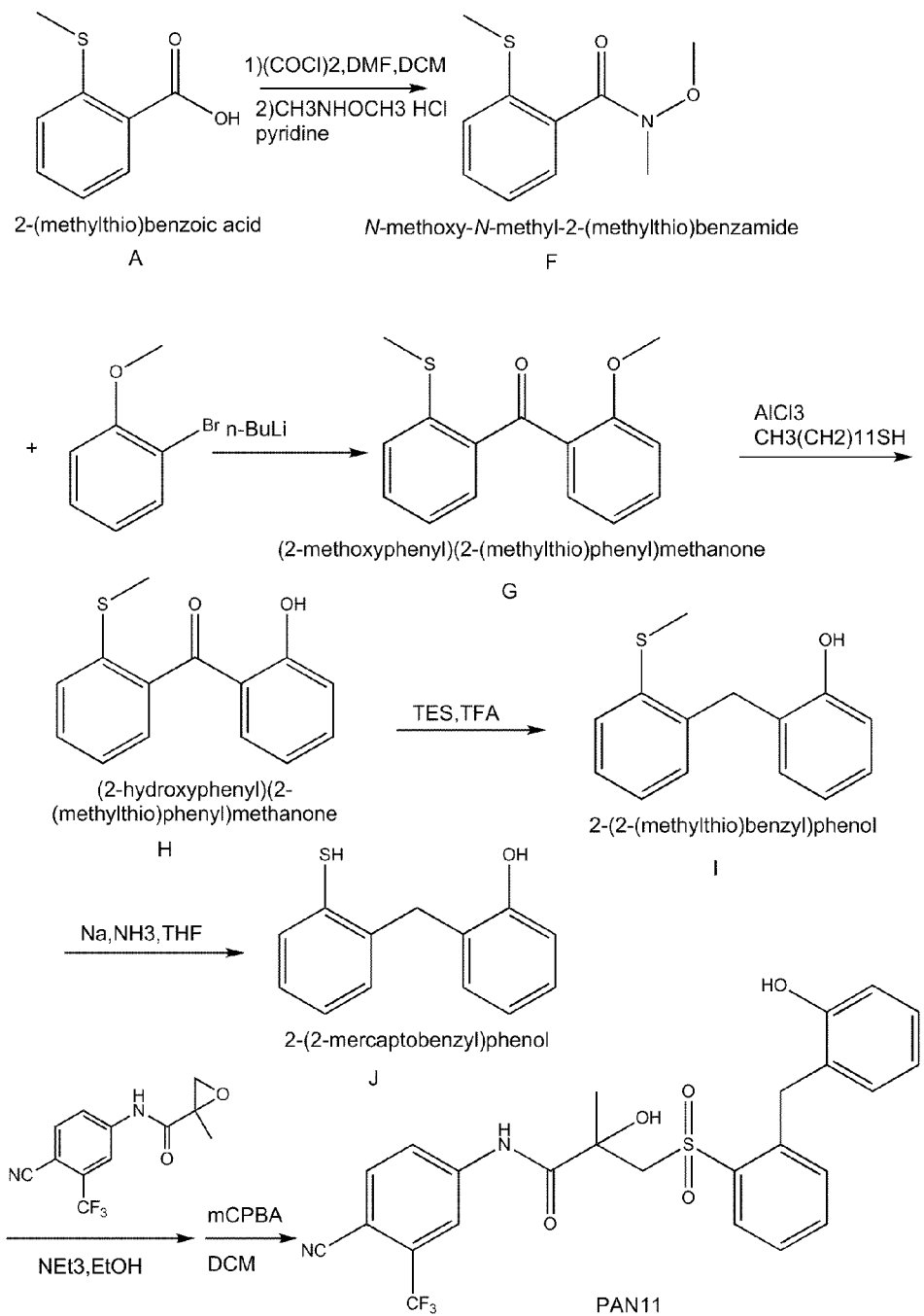
FIG. 10. General strategy for synthesis of PAN11.
Figure 11:
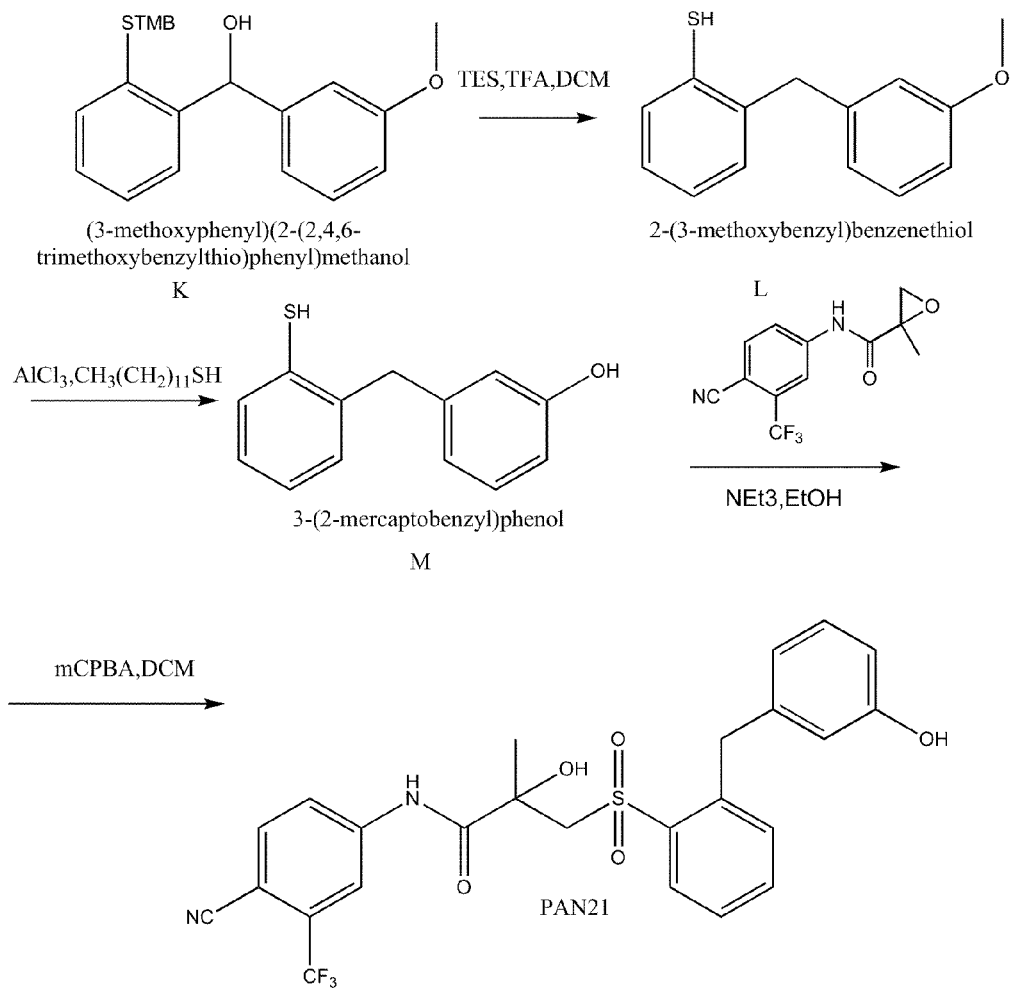
FIG. 11. General strategy for synthesis of PAN21.
Figure 12:
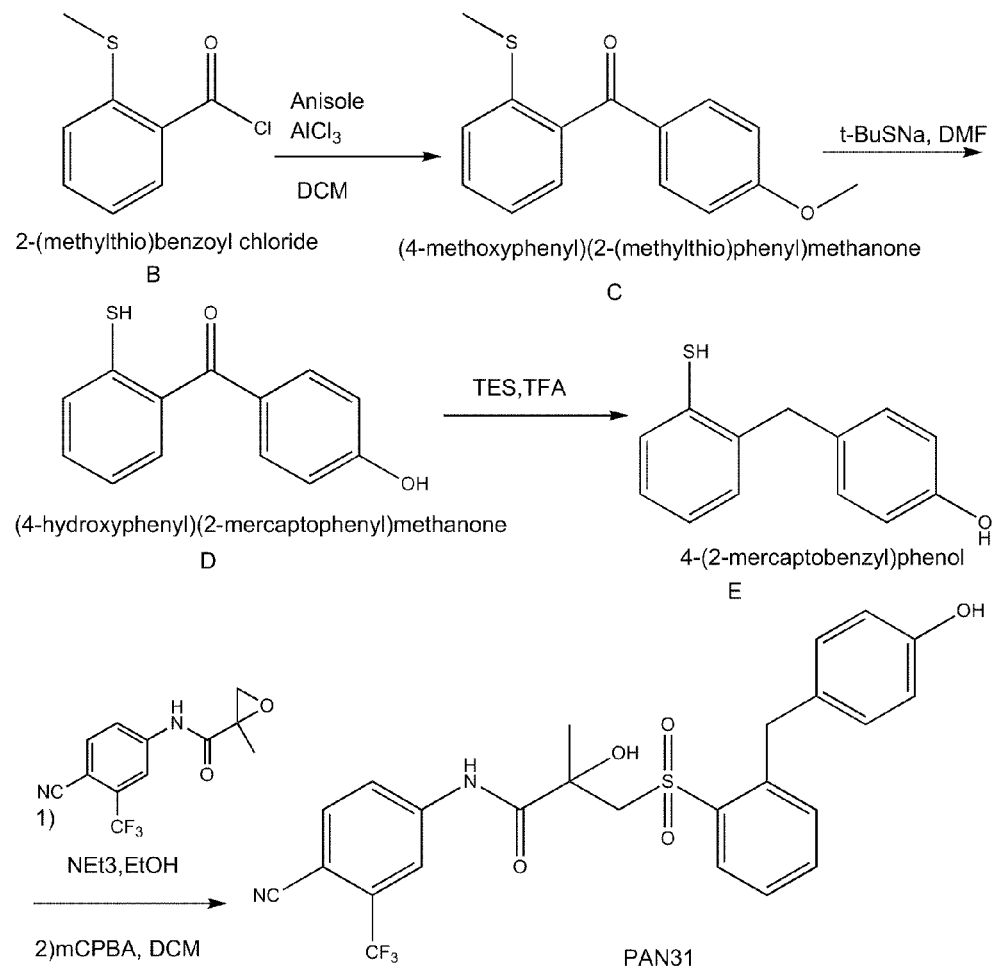
FIG. 12. General strategy for synthesis of PAN31.
Figure 13:
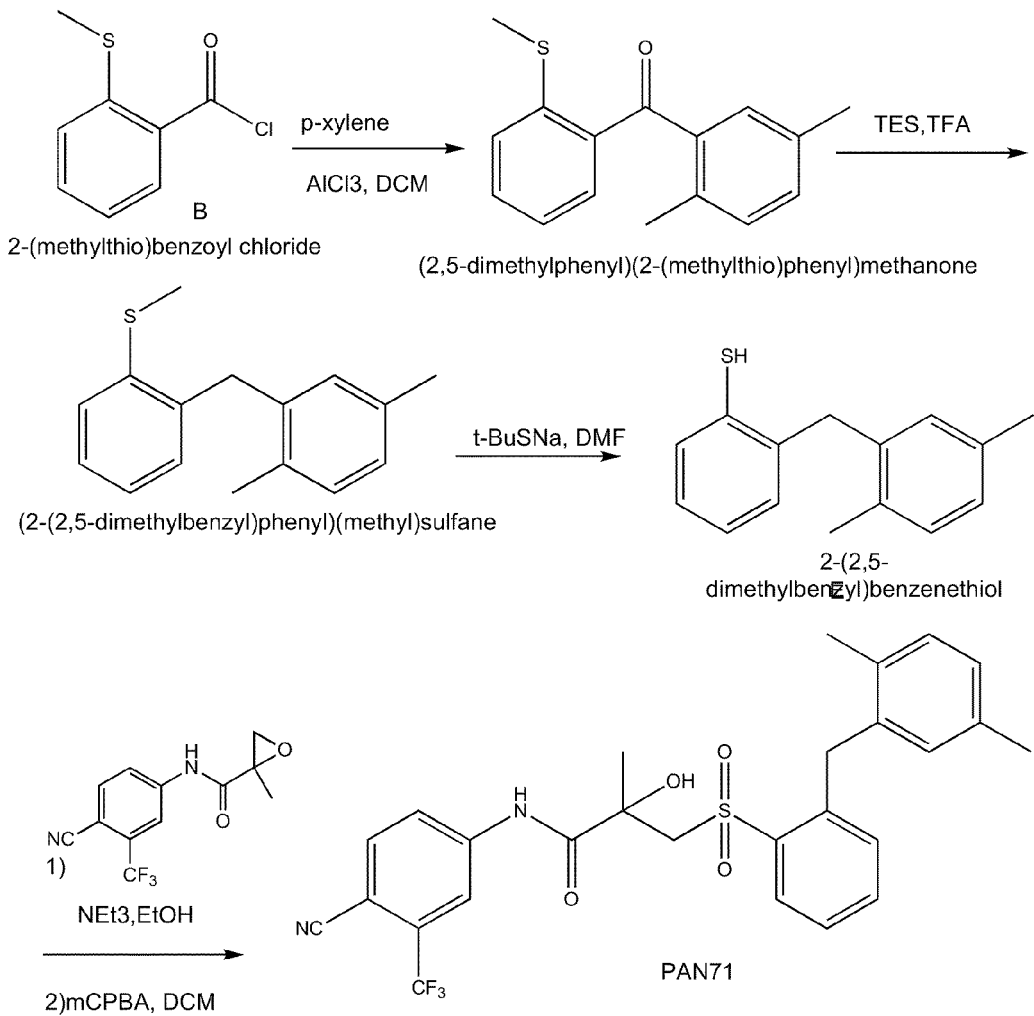
FIG. 13. General strategy for synthesis of PAN71.
Figure 14:
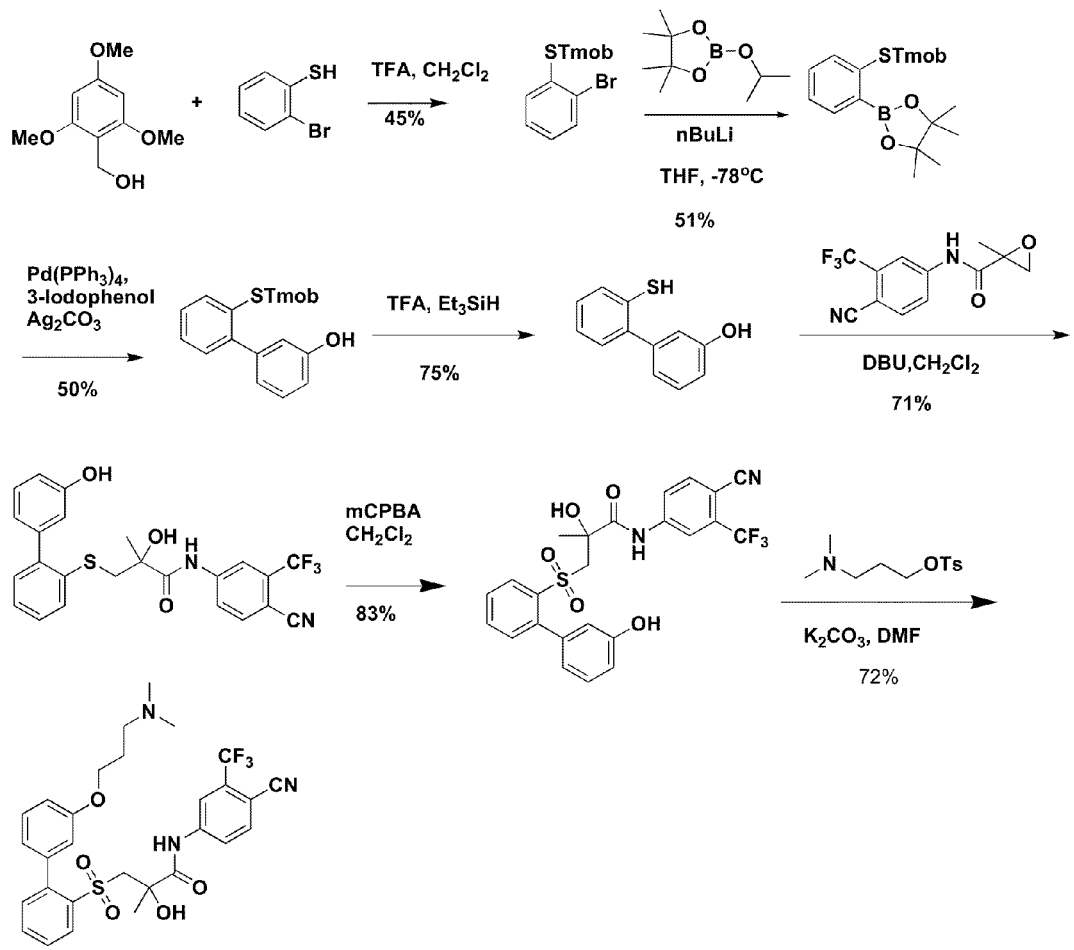
FIG. 14. Scale-up strategy for synthesis of PAN52.

25 mg (50 μmol) PAN11 (see FIG. 10 for structure), 42 mg (129 μmol) anhydrous cesium carbonate and 8 mg (50 μmol) 3-dimethylaminopropylchloride hydrochloride were mixed in 1 ml anhydrous DMF (dimethylformamide). The reaction mixture was stirred under nitrogen overnight. After reaction the mixture was extracted with ethyl acetate. The organic layer was separated, washed with water, brine and dried over magnesium sulfate, filtered and evaporated. The crude oil was partially refined by silica chromatography followed by purification by C4 HPLC (0.3 ml/min, acetonitrile/0.01% TFA water solution). HPLC separation yield 5.2 mg PAN42 (8.8 μmol, 17% yield). $^{13}$C NMR (101 MHz, MeOD) δ 175.25, 158.09, 144.05, 143.11, 139.66, 137.01, 134.89, 132.47, 131.86, 131.42, 129.47, 128.60, 127.59, 124.11, 121.86, 119.08, 117.70, 116.71, 112.59, 104.78, 101.41, 74.73, 66.75, 64.29, 57.15, 45.05, 34.03, 28.11, 27.71. $^{1}$H NMR (400 MHz, MeOD) δ 8.12 (s, 1H), 7.97-7.76 (m, 3H), 7.51 (t, J=6.9, 1H), 7.33 (d, J=7.8, 1H), 7.25 (d, J=7.4, 1H), 7.15 (t, J=8.0, 1H), 6.83 (s, 2H), 6.76 (d, J=6.1, 1H), 3.86 (d, J=6.4, 2H), 3.56 (d, J=14.8, 1H), 3.45 (t, J=6.4, 2H) 3.08 (d, J=14.8, 1H), 2.96 (s, 6H), 1.75 (d, J=6.4, 2H), 1.25 (s, 3H).

Example 2

Pan52 was Synthesized from (2-bromophenyl)(2,4,6-trimethoxybenzyl)sulfane

To a solution of (2-bromophenyl)(2,4,6-trimethoxybenzyl) sulfane 1.37 g (3.7 mmol) and 2-isopropoxy-4,4,5,5-tetramethyl-1,3,2-dioxaborolane 700 mg (3.7 mmol) in 37 ml THF at −78° C., was added dropwise 6.2 ml (7.4 mmol) of 1.2 M t-butyllithium. The reaction was allowed to stir at −78° C. for 45 min, before NH$_4$Cl was added and the resulting mixture extracted with ethyl ether (3× 15 ml). The organic layer was washed with brine (3× 15 ml) dried over MgSO$_4$ and concentrated in vacuo. The product, 4,4,5,5-tetramethyl-2-(2-(2,4,6-trimethoxybenzylthio)phenyl)-1,3,2-dioxaborolane, was crystallized from ether 0.8 g (52% yield) and was used in next reaction without further purification. $^{1}$H NMR (400 MHz, C$_6$D$_6$) δ 1.34 (s, 12H), 3.7 (s, 6H), 3.8 (s, 3H), 4.14 (s, 2H), 6.08 (s, 2H), 7.09-7.13 (m, 1H), 7.21-7.29 (m, 1H), 7.37-7.39 (m, 1H), 7.59 (m, 1H); 13C NMR (100 MHz, C6D6) δ24.8, 27.6, 55.3, 55.7, 83.84, 90.5, 106.9, 124.7, 129.6, 130.4, 134.9, 144.1, 159.1, 160.3; HRMS calcd for C$_{22}$H$_{29}$BO$_5$S (M$^+$+Na) 439.1726 found 439.1742.

A mixture of 4,4,5,5-tetramethyl-2-(2-(2,4,6-trimethoxybenzylthio)phenyl)-1,3,2-dioxaborolane (1.2 g, 2.9 mmol), 3-Iodophenol (0.65 g, 2.9 mmol), Ag$_2$CO$_3$ (0.82 g, 2.9 mmol) and Pd(PPh$_3$)$_4$ (0.16 g, 0.15 mmol) in 6 ml of THF was refluxed in the dark for 12 h. The reaction mixture was poured into H$_2$O and the resulting mixture extracted with ether. The organic layer was washed with brine (3×20 ml) and dried over MgSO$_4$ and concentrated. The residue was purified by silica flash chromatography (40/60, ethylacetate/hexane) to afford 2'-(2,4,6-trimethoxybenzylthio)biphenyl-3-ol.

N-(4-cyano-3-(trifluoromethyl)phenyl)-2-hydroxy-3-(3'-hydroxybiphenyl-2-ylsulfonyl)-2-methylpropanamide, PAN51, was prepared from the reaction of 2'-(2,4,6-trimethoxybenzylthio)biphenyl-3-ol and N-(4-cyano-3-(trifluoromethyl)phenyl)-2-methyloxirane-2-carboxamide in ethanol with triethylamine as described previously.

Pan52 was prepared from Pan51 as follows: To a solution of Pan51 (58 mg, 0.11 mmol) in 3.7 ml DMF was added Cs$_2$CO$_3$ (72 mg, 0.22 mmol). The mixture was stirred for 10 min before 0.57 ml (0.22 mmol) solution of 3-(dimethylamino)propyl 4-methylbenzenesulfonate (100 mg/ml) was a added. The mixture was stirred at room temperature overnight. The reaction was diluted with methylene chloride and washed with H$_2$O. Organic layer was washed with brine, dried over MgSO$_4$ and concentrated in vacuo. The residue was purified using silica flash chromatography (5/95 Methanol (saturated with NH$_3$)/methylene chloride) to yield 49 mg of Pan 52 (72% yield).

$^{13}$C NMR (101 MHz, MeOD) δ 175.01, 161.21, 143.98, 143.28, 141.37, 140.47, 136.97, 134.21, 133.99, 129.91, 129.66, 128.79, 125.29, 124.08, 122.52, 119.03, 118.98, 118.59, 116.68, 116.20, 104.79, 74.55, 68.13, 63.51, 58.12, 45.34, 27.95, 27.62. $^{1}$H NMR (400 MHz, MeOD) δ 8.20 (d, J=13.1, 1H), 8.02-7.87 (m, 2H), 7.85-7.79 (m, 1H), 7.56 (dt, J=7.5, 15.0, 1H), 7.41 (dt, J=6.0, 18.3, 1H), 7.26-7.06 (m,

3H), 6.86-6.78 (m, 2H), 3.81 (d, J=6.4, 2H), 3.71 (dd, J=2.6, 14.7, 1H), 3.41 (t, J=6.4, 2H), 3.34 (dd, J=14.7, 18.9, 1H), 2.89 (s, 6H), 1.82 (d, J=6.4, 2H), 1.31 (d, J=4.9, 3H).

Example 3

PAN62 (Formula X) is made in a similar procedure as PAN42:

$^{13}$C NMR (101 MHz, MeOD) δ 174.95, 160.42, 144.00, 143.24, 140.65, 137.00, 134.33, 134.31, 132.78, 132.29, 129.86, 128.68, 125.33, 124.12, 122.61, 119.05, 119.00, 116.72, 114.80, 104.80, 74.54, 67.03, 63.28, 57.32, 45.18, 27.81, 27.66. $^1$H NMR (400 MHz, MeOD) δ 8.10 (s, 1H), 7.95-7.77 (m, 3H), 7.49 (t, J=7.1, 1H), 7.32-7.18 (m, 4H), 6.75 (d, J=8.5, 2H), 3.89 (d, J=6.4, 2H), 3.43-3.47 (m, 3H), 3.00 (d, J=14.8, 1H), 2.86 (s, 6H), 1.79 (d, J=6.4, 2H), 1

PAN12 (Formula V) is made in a similar procedure as PAN42

$^1$H NMR (400 MHz, MeOD) δ 7.97 (d, J=1.8, 1H), 7.93 (d, J=8.0, 1H), 7.76 (dd, J=1.8, 8.5, 1H), 7.66 (d, J=8.5, 1H), 7.36 (t, J=7.6, 1H), 7.21-7.05 (m, 4H), 6.86 (dd, J=7.7, 14.2, 2H), 4.37 (q, J=16.5, 2H), 4.21 (d, J=14.6, 1H), 3.81-3.64 (m, 3H), 3.41 (d, J=6.3, 2H), 2.95 (s, 6H), 1.82 (d, J=6.3, 2H), 1.55 (s, 3H). $^{13}$C NMR (101 MHz, CDCl3) δ 175.25, 158.09, 144.05, 143.11, 140.05, 137.01, 134.96, 133.69, 133.52, 133.12, 131.42, 129.47, 128.60, 127.59, 124.82, 121.86 117.70 116.71, 112.59, 104.78, 101.41, 74.73, 66.75, 64.29, 57.15, 45.05, 34.03, 28.11 27.71.

PAN22 (Formula VI) is made in a similar procedure as PAN42

$^1$H NMR (400 MHz, MeOD) δ 8.00 (d, J=8.2, 1H), 7.92 (d, J=8.0, 1H), 7.80 (d, J=8.5, 1H), 7.68 (d, J=8.5, 1H), 7.46 (t, J=7.5, 1H), 7.32-7.18 (m, 2H), 7.11 (t, J=7.8, 1H), 6.70 (dd, J=6.0, 13.3, 3H), 4.38 (q, J=15.7, 2H), 3.83-3.71 (m, 3H), 3.50 (d, J=6.4, 2H), 3.23 (d, J=14.5, 1H), 2.98 (s, 6H), 1.79 (d, J=6.4, 2H), 1.48 (s, 3H). $^{13}$C NMR (101 MHz, MeOD) δ 173.72, 158.38, 142.82, 141.86, 138.95, 137.08, 136.29, 135.97, 135.47, 133.76, 132.89, 132.44, 130.76, 127.47, 123.79, 122.60, 117.61, 117.56, 115.21, 103.28, 73.21, 65.99, 62.19, 56.13, 44.22, 35.67, 26.94, 26.36.

PAN38 (Formula VII) is made in a similar procedure as PAN42

$^1$H NMR (400 MHz, MeOD) δ 8.17 (d, J=2.0, 1H), 7.89 (d, J=8.2, 2H), 7.79 (d, J=8.5, 1H), 7.34 (dd, J=6.9, 8.2, 1H), 7.21 (t, J=7.7, 1H), 7.11 (d, J=7.7, 1 H), 6.94 (d, J=8.6, 2H), 6.66-6.60 (m, 2H), 4.33-4.22 (m, 2H), 3.82-3.79 (m, 3H), 3.41 (d, J=6.3, 2H), 3.25 (d, J=14.7, 1H), 3.00 (s, 6H), 1.77 (d, J=6.3, 2H), 1.32 (s, 3H). $^{13}$C NMR (101 MHz, MeOD) δ 171.78, 157.51, 141.90, 141.32, 137.17, 135.66, 134.42, 134.36, 132.86, 131.27, 130.63, 130.58, 130.47, 130.44, 129.97, 127.52, 123.32, 114.72, 114.67, 74.28, 66.53, 61.31, 56.09, 45.84, 37.36, 27.79, 26.16.

Example 4

Transcription Assays

Twenty-four hours prior to transfection, CV-1 cells were seeded at a density of 45,000 cells per well in 24-well cell culture plates and grown in phenol red free Dulbecco's Modified Eagle Medium (DMEM) supplemented with 10% cosmic calf serum (COS). ARE-luciferase reporter and Renilla-Luc as the internal standard and a prokaryotic expression vector encoding the wild-type androgen receptor or mutant androgen receptor were transfected with Lipofectamine (Invitrogen) following manufacturer's protocol. Five hours after transfection, media was added containing the appropriate concentrations of ligands. The cells were allowed to incubate for 38 hours before harvesting by passive lysis buffer. Cell extracts were immediately assayed using the Dual Luciferase Assay (Promega) with a Perkin-Elmer Microbeta Luminometer. Activity is reported in relative light unit (RLU), determined as the ratio of inducible firefly luciferase luminescence divided by the luminescence of the renilla luciferase control normalized to 10 nM DHT in hAR(wt). Dose-response data was analyzed by nonlinear regression analysis using GraphPad Prism. See Table 1 for results.

TABLE 1

Cellular reporter gene activities of analogues alone and in competition with DHT.

| | AR wt | | AR T877A | | AR W741C | | AR W741L | |
| --- | --- | --- | --- | --- | --- | --- | --- | --- |
| Ligands | $EC_{50}$ (μM) | $IC_{50}$ (μM) | $EC_{50}$ (μM) | $IC_{50}$ (μM) | $EC_{50}$ (μM) | $IC_{50}$ (μM) | $EC_{50}$ (μM) | $IC_{50}$ (μM) |
| bic (control) | 1.0 ± .08 | | 1.9 ± 0.4 | | 0.107 ± 0.02 | | 0.052 ± 0.014 | |
| PAN12 (Formula V) | — | 2.4 (59%) | — | 4.1 ± 0.7 (53% ± 5.6%) | — | — | — | — |
| PAN22 (Formula VI) | — | 2.0 ± 2.2 (50% ± 30%) | — | 1.8 ± 0.3 (53% ± 3.8%) | — | 5.6 ± 0.8 (53% ± 2.1%) | — | 3.0 ± 1.8 (52% ± 4.9%) |
| PAN38 (Formula VII) | — | — | — | — | — | — | — | — |
| PAN41 | — | 1.2 ± 0.5 (45% ± 14%) | — | 3.9 ± 1.9 (53% ± 10%) | — | 8.0 ± 2.6 (50% ± 1.0%) | — | 5.8 ± 1.6 (50% ± 1.0%) |
| PAN42 (Formula VIII) | — | — | — | — | — | — | — | — |
| PAN52 (Formula IX) | — | 3.5 ± 2.0 (49% ± 4.4%) | — | 4.0 ± 2.2 (52% ± 2.5%) | — | 5.9 ± 2.5 (50% ± 1.0%) | — | 12.2 ± 6.2 (53% ± 5.2%) |
| PAN 62 (Formula X) | — | 2.3 ± 0.9 (51% ± 9.1%) | — | 5.0 ± 3.2 (56% ± 5.9%) | — | 15 ± 17 (56% ± 5.7%) | — | 11 ± 11 (62% ± 12%) |

'bic' = bicalutamide. $EC_{50}$ = effective concentration for half maximal activation of reporter gene expression. $IC_{50}$ = 50% inhibitory concentration of cellular reporter gene expression induced by 3 nM, 250 nM, 200 nM or 10 nM DHT for wild-type, W741L, W741C and T877A respectively. PAN41 = N-(4-cyano-3-(trifluoromethyl)phenyl)-2-hydroxy-3-(2'-hydroxybiphenyl-2-ylsulfonyl)-2-methylpropanamide. Values are reported as the average of three independent experiments run in triplicate ± sem (standard error of the mean). 'nd' indicates values were not determined, and '—' indicates no effect. Antagonist efficacy was defined as RLU (relative light units) value at $IC_{50}$.

Cell based reporter gene assays show that the analogs are potent antagonists in cells expressing AR mutants that cause bicalutamide to be agonists.

Example 5

Competitive Binding Assays

Twenty-four hours prior to transfection, COS-7 cells were seeded at a density of 70,000 cells per well in 24-well cell culture plates and grown in phenol red free Dulbecco's Modified Eagle Medium (DMEM) supplement with 10% cosmic calf serum (CCS). The cells were transfected with a prokaryotic expression vector encoding the wild-type androgen receptor or mutant androgen receptor using Lipofectamine (Invitrogen) following manufacturer's protocol. The cells were allowed to grow for 30 hours and then labeled for 2 hours at 37° C. with [$^3$H]DHT and the appropriate concentration of ligands. Cells were washed with PBS and harvested in 2% SDS, 10% glycerol, and 10 mM Tris, pH 6.8, and radioactivity determined by scintillation counting. See Table 2 for results.

TABLE 2

Extended Panantagonist Binding Affinities.

| Ligand | AR wt ($\mu$M) | AR T877A ($\mu$M) | AR W741C ($\mu$M) |
|---|---|---|---|
| Bicalutamide | 0.8 | 0.051 | 0.24 |
| PAN12 | 5.8 | 2.6 | 16 |
| PAN22 | 2.3 | 1.75 | 9.8 |
| PAN52 | 3.0 | 4.13 | 7.3 |
| PAN62 | 25 | 4.3 | 2.62 |

Competitive binding assay (Ki) were measured in the presence of 8 nM, 14 nM and 75 nM [3H]-DHT for AR (wild-type), AR (T877A) and AR (W741C) respectively.

Radioligand displacement binding assays confirm that compounds are competitive for DHT binding to AR.

Example 6

Cytotoxicity Assays

Viability of LNCaP cells in the presence of bicalutamide and PAN52 were determined by Live/Dead® (Molecular Probes, Invitrogen) cell viability assay kit following manufacturer's protocol. LnCaP cells are seeded at 45,000 per 32 mm dish and grown in RPMI supplemented with 10% DCC-FBS in the presence of PAN52 or bicalutamide. Media was changed every 3 days and floating cells were centrifuged down and reseeded into dish. LIVE/DEAD reagent was added after 9 days culturing. Live cells (indicated by green fluorescence) were counted and compared to the number of dead cells (red). Bicalutamide and PAN52 have similar cellular toxicities at 1 $\mu$M indicating that differences in cellular behavior induced by PAN52 (versus bicalutimde) at 1 $\mu$M are not due to indiscriminate cell toxicity. See FIG. 1.

Example 7

Clonogenic Assays

Figure 2:
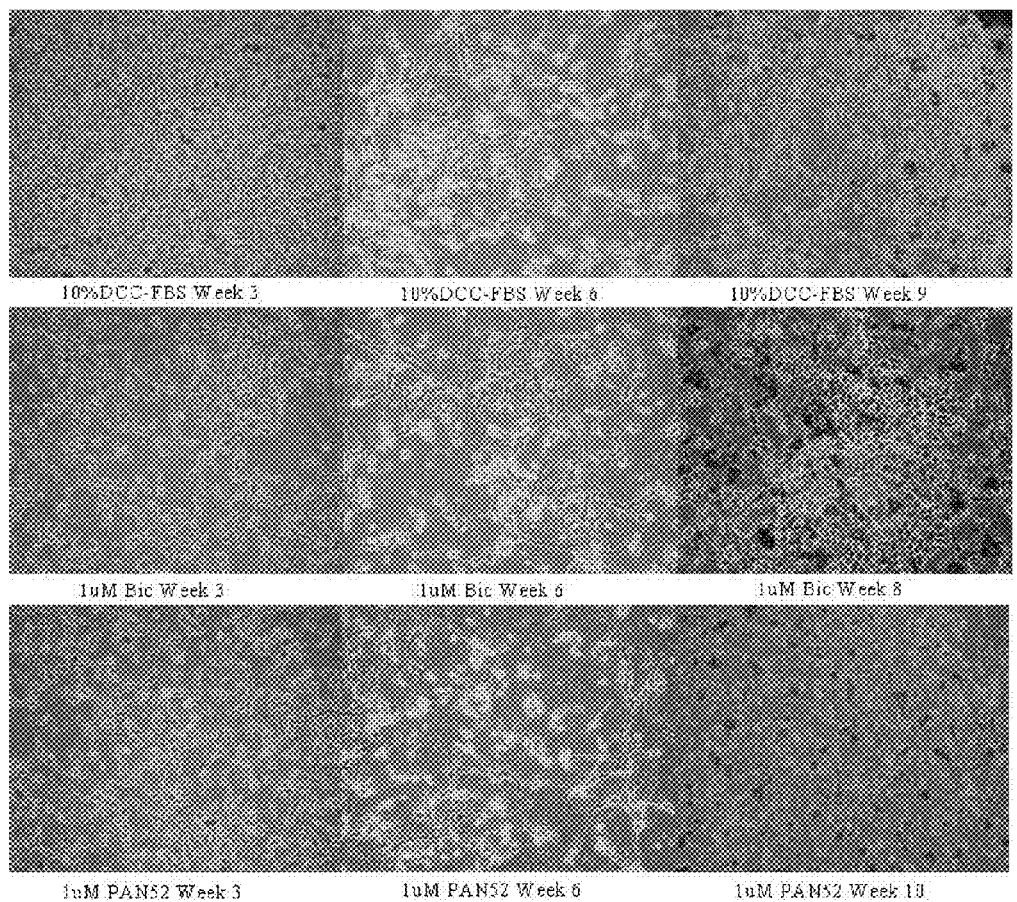
FIG. 2. LnCaP clonogenic assay comparing bicalutamide and PAN52 at 1 µM in RPMI+10% DCC-FBS. The media was changed every three days.

Clonogenic assays are performed by a modification of the procedure described by Nara et al. (Cancer Research 2003, 63, 149-153). LNCaP cells were seeded at a density of 80,000 cells per well in 6-well cell culture plates and maintained in 3 ml phenol red free RPMI 1640 with 10% DCC-FBS in the presence and absence of 1 $\mu$M ligands, bicalutamide and PAN52. Media was changed every three days was and documented weekly. If cells reach 95% confluence, the cells were counted and reseeded at a density of 80,000 cell per well. See FIG. 2.

Example 8

Long-Term Cell Proliferation Assays

Figure 3:
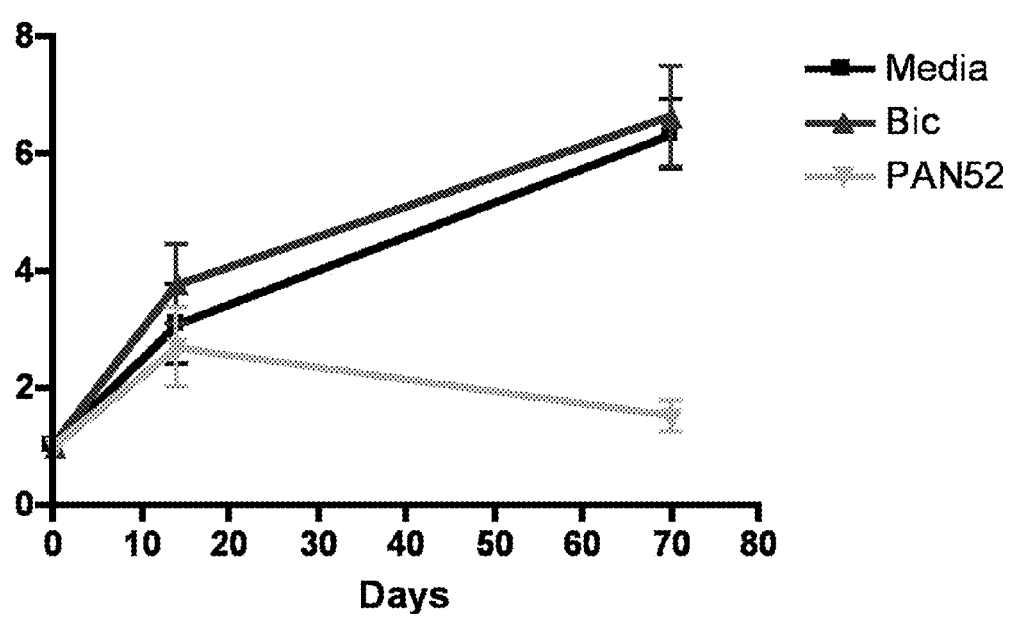
FIG. 3. Long-term cell proliferation assay comparing bicalutamide (1 µM), PAN52 (1 µM), and Media control (no ligand) in RPMI+10% DCC-FBS.

LNCaP cells were seeded at a density of 80,000 cells per well in 6-well cell culture plates and maintained in 3 ml phenol red free RPMI 1640 with 10% DCC-FBS in the presence and absence of 1 $\mu$M ligands, bicalutamide and PAN52. Media was changed every three days. Cell numbers was counted at by hemacytometer. Cell number is reported in relative cell number, determined as the ratio of cell numbers divided by the number seeded (80,000 cells/well). See FIG. 3.

Example 9

Assessment of Mode of Action by Nuclear Localization

As essentially all AR dependent signaling paradigms require AR to enter the nucleus, it is generally believed that reducing AR localization in the nucleus as a readout for antiandrogen action could be effective in blocking multiple AR resistance mechanisms including AR overexpression, gain-of-function mutations and outlaw pathways. Applicants evaluated PLM1, PLM6 and Pan52 in CV-1 cells expressing GFP-AR. CV-1 monkey kidney cells were seeded in a 12 well plate at a concentration of 50,000 cells per well. After 24 h, the cells were transfected with GFP-AR in a solution of Opti-MEM and Lipofectamine 2000, and incubated overnight. The cells were then imaged on a fluorescent microscope, followed by the addition of 6 respective ligands, and control (DMSO vehicle). The ligand concentrations in the wells were 10 $\mu$M for DHT and 100 $\mu$M for all other ligands. The cells were incubated for two hours and again imaged. The cells were fixed, and stained (DAPI) to image the nucleus.

Figure 4:
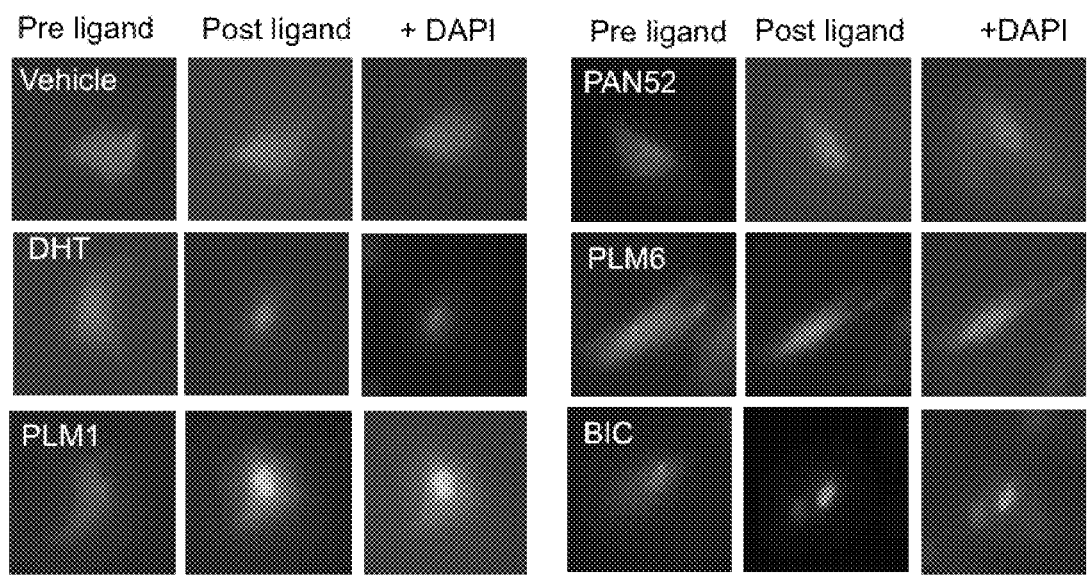
FIG. 4. Nuclear localization of GFP-AR in CV-1 cells grown in 10% charcoal stripped CCS/DMEM. Pre-ligand; before addition of ligand, Post ligand GFP fluorescence 2 h after ligand addition (DHT at 10 nM and antagonists at 100 nM), +DAPI; overlay with DAPI nuclear stain.

As shown in FIG. 4, in the absence of ligand (in hormone depleted media), GFP-AR is diffuse throughout the nucleus and cytoplasm; however, upon treatment with the agonist DHT or the antagonists mifepristone or bicalutamide, GFP-AR fluorescence localizes almost exclusively within the nucleus. By contrast, cells treated with PLM6 or Pan52 show little to no nuclear localization. The response to PLM1 is more intermediate showing partial localization in the nucleus but clear cytoplasmic fluorescence as well.

These studies establish that PLM1, PLM6 and Pan52 function differently from known antagonists in their ability to localize GFP-AR. Reduced nuclear localization may contribute to the ability of PLM6 and Pan52 (but not bicalutamide and PLM1) to evade resistance in vitro selections.

Example 10

Assessment of MOA by In Vitro Co-Factor Recruitment

Peptide probes that bind selectively to AR in the presence of certain but not all AR ligands have been used as a means to evaluate and classify agonists and antagonists of similar function. Applicants examined the ability of antagonists to mediate coactivator peptide (D11, FXXLF) by TR-FRET using Tb labeled AR ligand-binding domain (LBD) and fluorescein labeled peptide (Invitrogen; #PV8431) following manufacture's protocol. Briefly, serial dilutions of ligand stocks solutions (in DMSO) were made in TR-FRET coregulator buffer A in a 384 well plate. To each well was added a 4x-stock solution of the AR-LBD followed by a 4x stock solution of fluorescein D-11 peptide and lanthanide-labeled antiGST antibody. The plates were read by time resolved fluorescence after 2 h and 4 h incubation.

Figure 5:
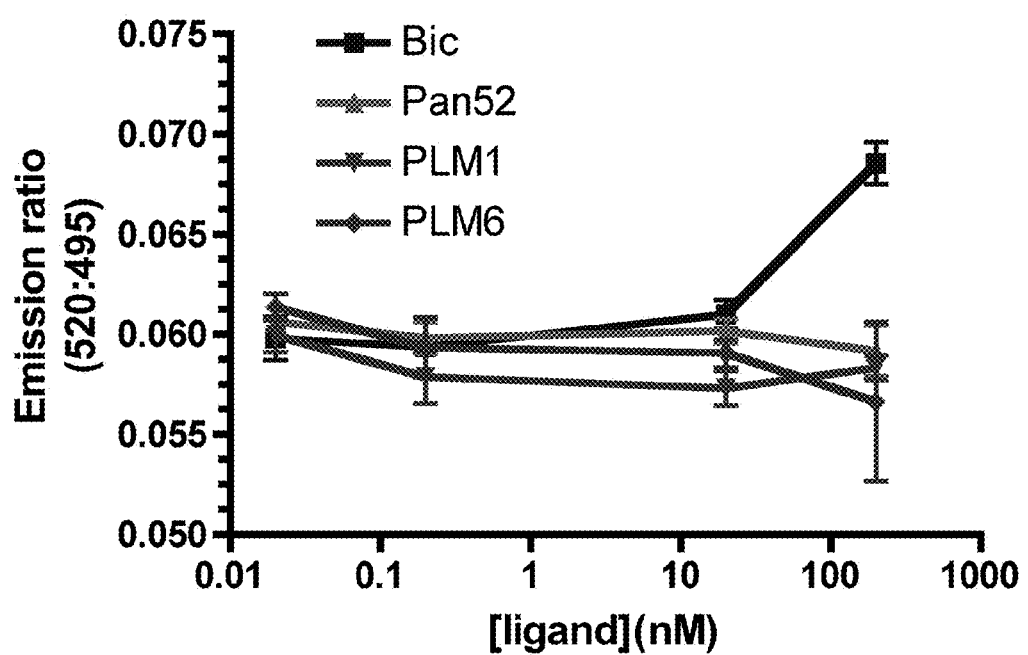
FIG. 5. Coactivator recruitment by TR-FRET (Time-Resolved Fluorescence Resonance Energy Transfer).

Applicants observed association of coactivator peptide in the presence of nanomolar concentrations of DHT. Reminiscent of the ability of high concentrations of bicalutamide to act as an agonist in AR over-expressing cells, Applicants observed coactivator association to bicalutamide-liganded AR(LBD) similar to reported studies. By contrast PLM1, PLM6 and Pan52 do not show coactivator association in these concentrations (FIG. 5).

Taken together nuclear localization (Example 9) and coactivator association (Example 10) assays demonstrate that PLM1, PLM6 and Pan52 interact with AR in a fundamentally different manner than the current repertoire of clinically used AR antagonists.

Example 11

Multi-Dose In Vivo Toxicology and Assessment of Tissue Specific Response

Figure 6:
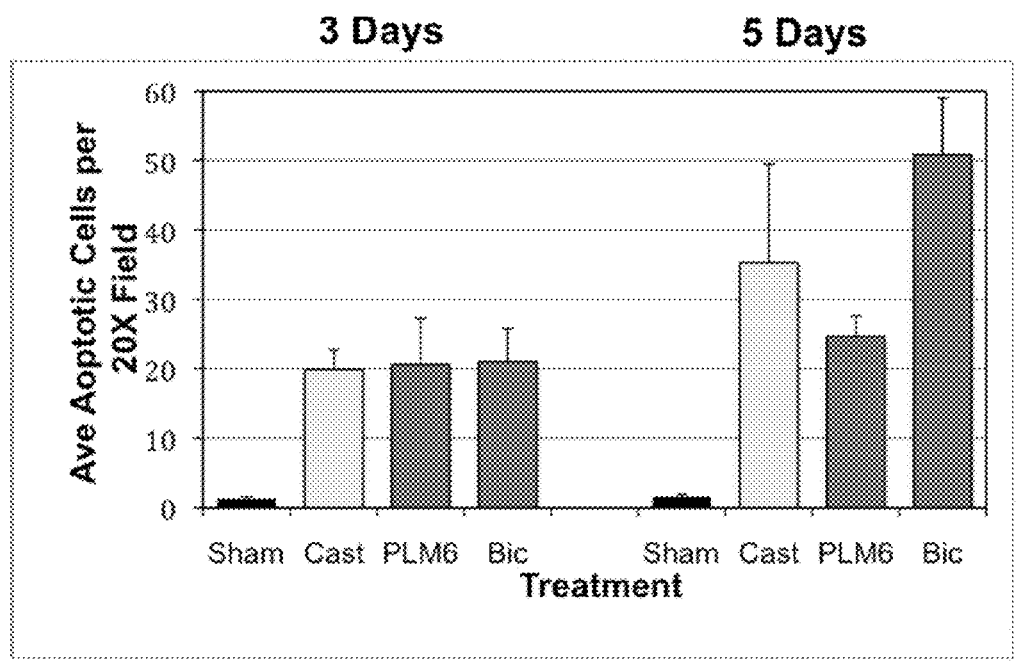
FIG. 6. Quantification of apoptotic cells from prostate tissues where mice were either sham-castrated, castrated or treated short-term by intraperitoneal injection with PLM6 or Bicalutamide (Bic) at 25 mg/kg/day for either 3 days (left) or 5 days (right). Single 20× magnification fields from each of four lobes of mouse prostate glands were counted in each mouse. PLM6 induces rapid apoptosis in mouse prostates consistent with castration and bicalutamide, and all time points are significantly different from sham-castrated controls. PLM6 data represents 3 mice at day 3 and 2 mice at day 6 due to toxicity at 25 mg/kg while bicalutamide data are from two mice from each time point. Data are expressed as means±SE. Statistics were determined using two-tailed, paired t-tests assuming data from each lobe was independent.

Male C57BI/6 mice were divided into four groups: sham castrates, castrates, and drug treated; PLM6 (N=3 at two time points) or bicalutamide (N=3 at two time points). PLM6 and bicalutamide were injected IP as 9:1 peanut oil: antagonist (resuspended in ethanol) at 25 mg/kg/day in intact mice (not castrated). Under these conditions, no abnormal behavior in grooming or feeding was observed for either the 3 d or 5 d course. Weight loss was observed but did not approach 10% of body weight. There was 1 death (⅙) with PLM6 at 5 days of treatment and two deaths in the bicalutamide groups. Prostates were removed from 3 day and 5 day treatment groups, sectioned and stained by H&E and TUNEL. PLM6 and bicalutamide showed a significant increase in apoptosis as compared to sham-operated controls at both day 3 and day 5 with apoptosis increasing in all groups from day 3 to day 5 (FIG. 6, TUNEL).

Figure 7:
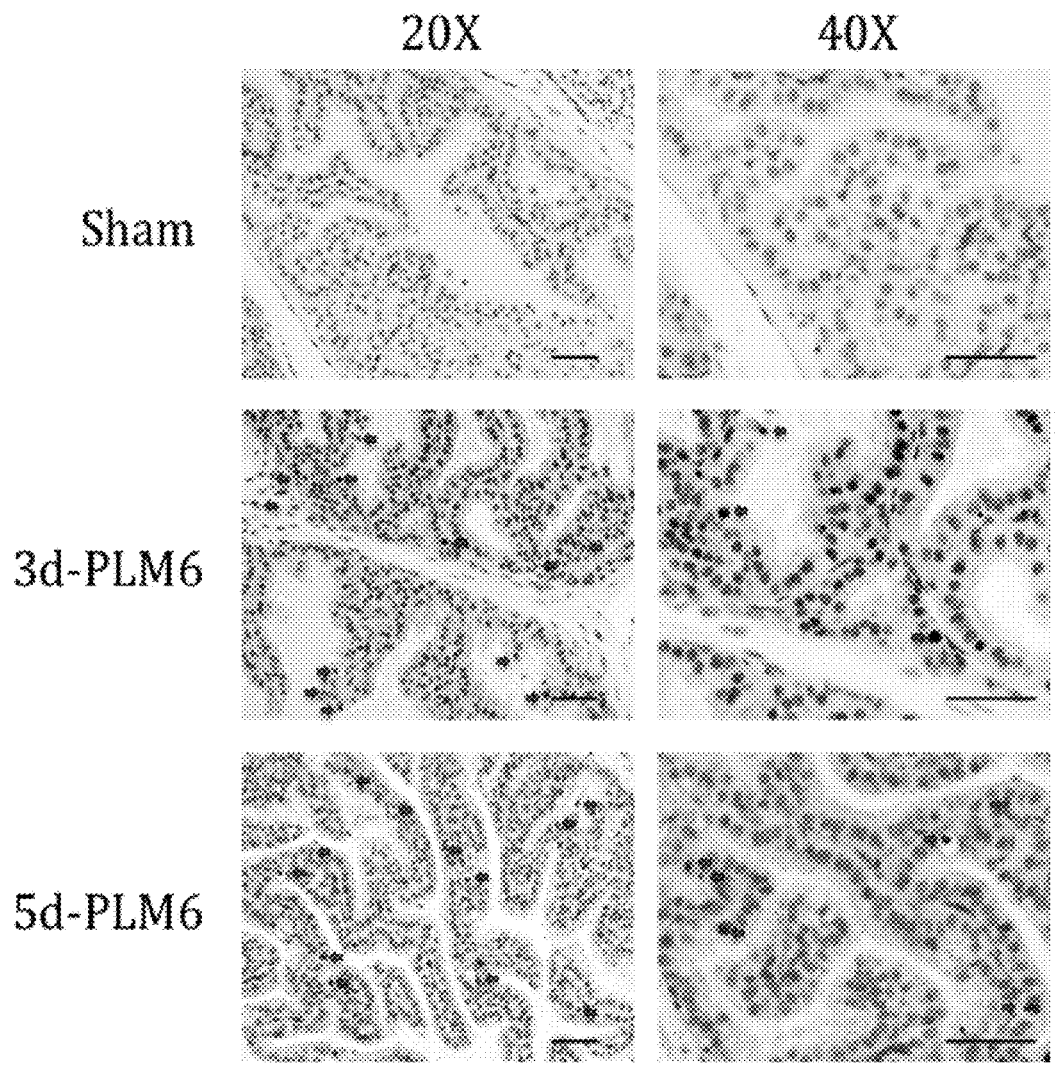
FIG. 7. Representative TUNEL assays for Sham (Vehicle treated) and PLM6 treated mouse prostate sections used for quantification in FIG. 3. Left side is 20× magnification with apoptotic nuclei indicated by arrows where brown staining present from TUNEL reaction. Right side is 40× from the same 20× field. Scale bars are 50 µm.
Figure 8:
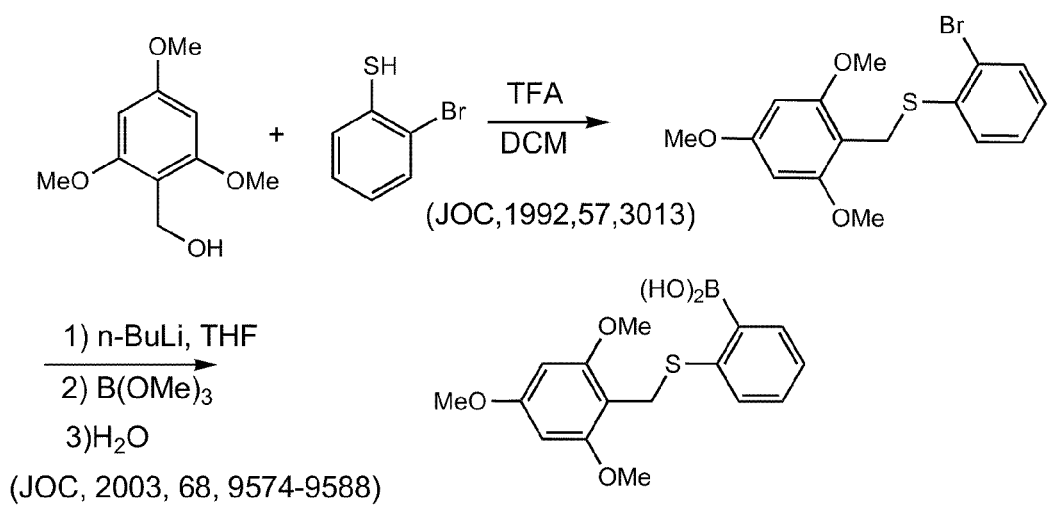
FIG. 8. Synthetic scheme for construction of precursors for PAN41, PAN51, PAN61 (see Published U.S. Patent Application No. 2008/0064757).
Figure 9:
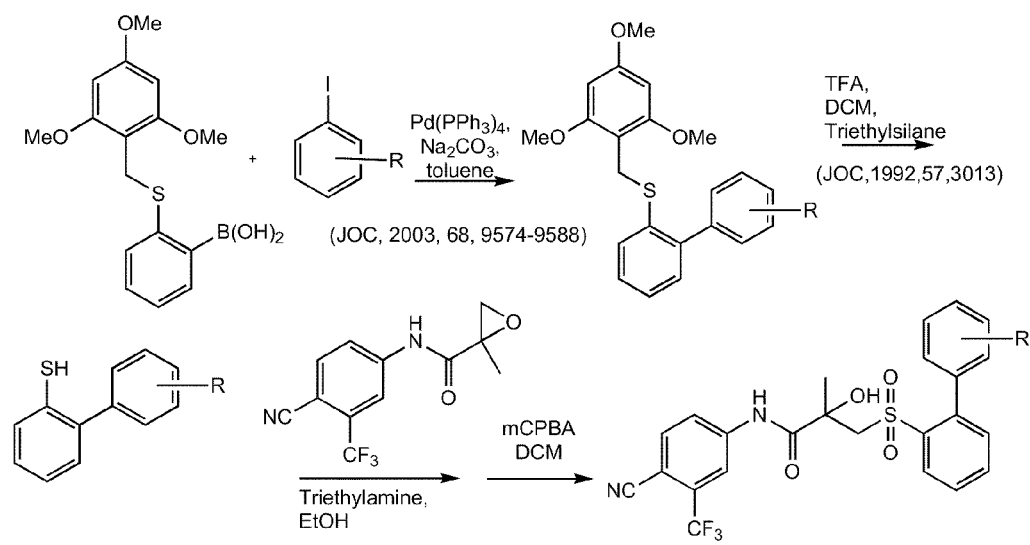
FIG. 9. General strategy for synthesis of PAN41, PAN51, PAN61.

PLM6-induced glandular apoptosis was 19.9±2.8 cells per 20x field on day 3 (P=0.0064) that reached 24.63±3 cells per 20x field on day 5 (P=$2.59 \times 10^{-4}$) (FIG. 7). Prostates from treated and control mice were isolated, fixed sectioned and stained TUNEL (BrdU). Sections were then evaluated by visible light microscopy and counting.

The actions of bicalutamide also were performed (FIG. 7). Bicalutamide had 21.04±4.7 cells per 20x field (P=0.00014). This value is indistinguishable from PLM6. Five days Bic treatment resulted in 50.83±8.2 cells per 20x field. This value is slightly more than twice that observed in PLM6 treated prostates at day 5.

Example 12

Assessment of AR Downregulation

Figure 15:
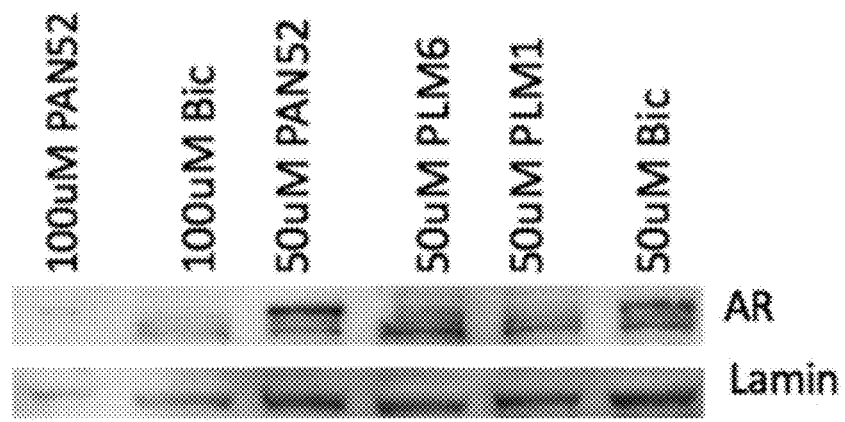
FIG. 15. Western blot analysis (IB: Anti-AR versus Anti Lamin) of SDS PAGE gel of LNCaP lysates after treatment with 100 µM Pan52 and Bicalutamide (Bic) and 50 µM Bicalutamide, PLM1, PLM6 PAN52.
Figure 16:
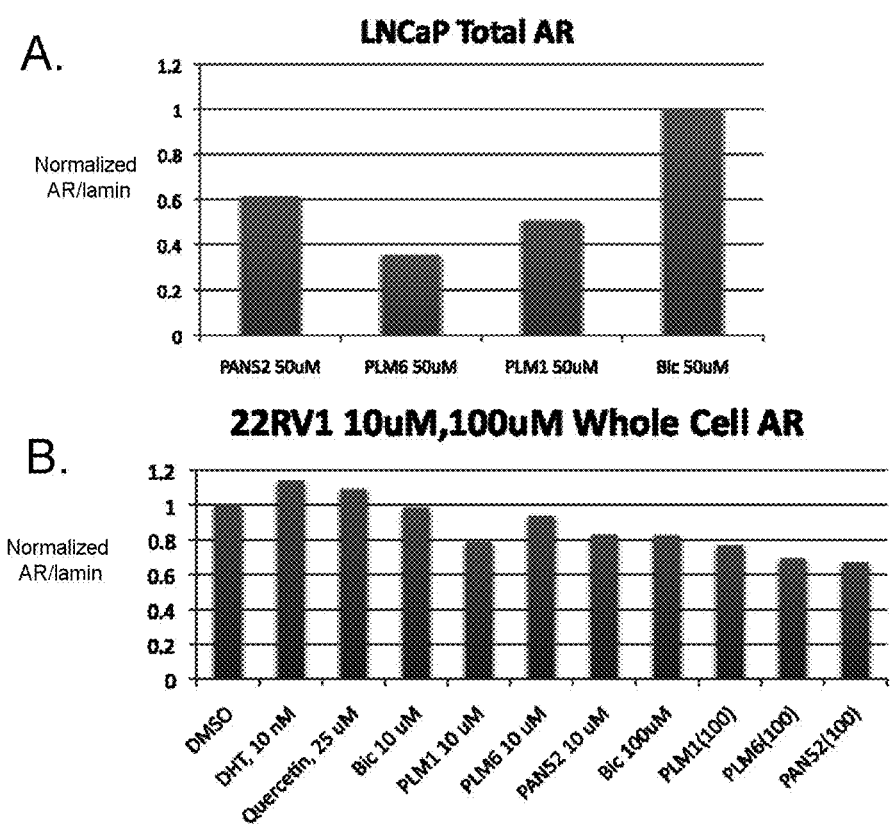
FIG. 16. Quantitative analysis of relative AR levels relative to lamin controls assessed by densitometry analysis of western blots (IB: anti-AR versus anti-lamin) of SDS PAGE gels of cell lysates from A. LNCaP cells treated with 50 µM PAN52, PLM6, PLM1 and Bic. B. CWR22RV cells treated with DHT, vehicle or 10 µM or 100 µM anti-androgen.

Compounds that down regulate the levels of AR in prostate cancer may be effective in androgen dependent cells and anti-androgen resistant cells that over express the androgen receptor. Applicants observed downregulation of AR protein levels in LNCaP and CRW22 cells upon treatment with PLM1, PAN52, PLM6 relative to bicalutamide, DHT or DMSO controls. LNCaP or CRW22RV1 cells were treated with 10 µM, 50 µM or 100 µM compound for 24 h. Cells were harvested and lysed. Cell lysates were analyzed by SDS-PAGE followed by immunostaining with anti-AR and anti-lamin antibodies (see FIGS. 15 and 16).

Example 13

Figure 17:
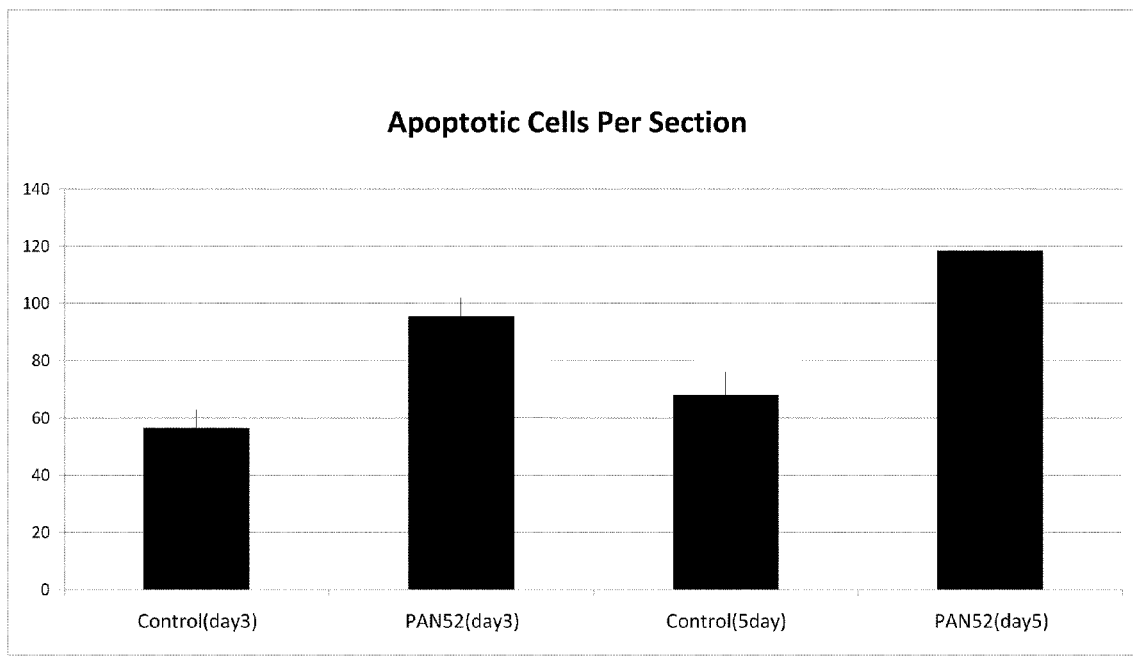
FIG. 17. Quantification of apoptotic cells from prostate tissues where mice were treated short-term by intraperitoneal (IP) injection with PAN52 at 25 mg/kg/day versus vehicle control for either 3 days or 5 days (right). Single 20× magnification fields from each of four lobes of mouse prostate glands were counted in each mouse. PAN52 induced rapid apoptosis in mouse prostates.
Figure 18:
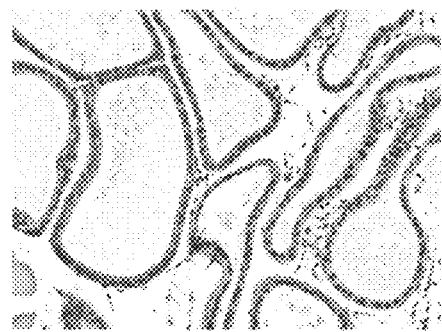
FIG. 18. Representative TUNEL assays for Sham (Vehicle treated) and PAN52 treated mouse prostate sections used for quantification in FIG. 17. 20× magnification with apoptotic nuclei indicated by arrows where brown staining present from TUNEL reaction.
Figure 18:
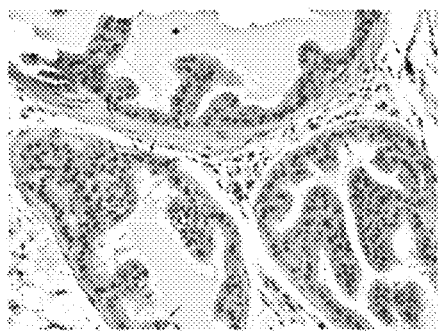
Figure 18:
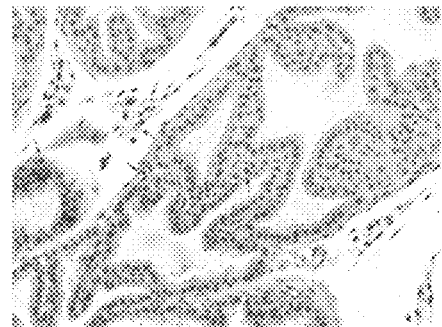
Figure 18:
Figure 18:
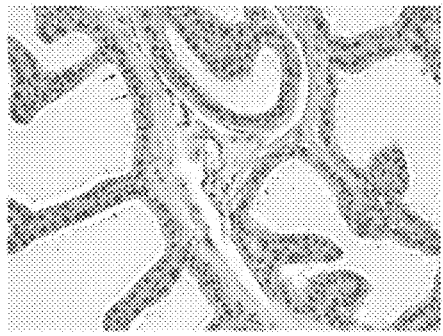

Male C57Bl/6 mice were treated with PAN52 or vehicle (ethanol) injected IP as 9:1 Cremophor: antagonist (resuspended in ethanol) at 25 mg/kg/day in intact mice (not castrated). Under these conditions, no abnormal behavior in grooming or feeding was observed for either the 3 day or 5 day course. Prostates were removed from 3 day and 5 day treatment groups, sectioned and stained by H&E and TUNEL. PAN52 showed an increase in apoptosis as compared to control at both day 3 and day 5 (see FIGS. 17 and 18).

We claim:

1. A compound of the formula:

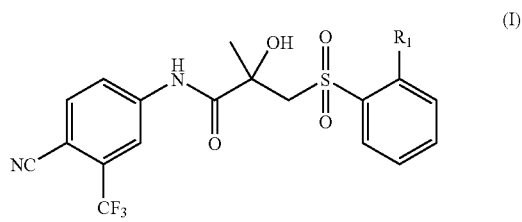

wherein $R_1$ is phenyl phenoxy, benzoyl, phenylthio or benzyl, said $R_1$ being substituted with alkyl, branched alkyl, alkoxy, branched alkoxy, aryl, aryloxy, alkylamido, alkylcarbamoyl, or acyl; said provided that, when $R_1$ is substituted with alkyl or branched alkyl, the alkyl or branched alkyl is further substituted with amino, alkylamino, dialkylamino, arylamino, acyl, ester, carboxyl, hydroxyl, alkoxy, sulfonyl or cyano; further provided that, when $R_1$ is substituted with alkoxy, branched alkoxy, aryl, aryloxy, alkylamido, alkylcarbamoyl, or acyl, the alkoxy, branched alkoxy, aryl, aryloxy, alkylamido, alkylcarbamoyl, or acyl is further optionally substituted with alkyl, amino, alkylamino, dialkylamino, arylamino, acyl, ester, carboxyl, hydroxyl, alkoxy, sulfonyl or cyano.

2. The compound of claim 1, wherein said compound is selected from the group consisting of:

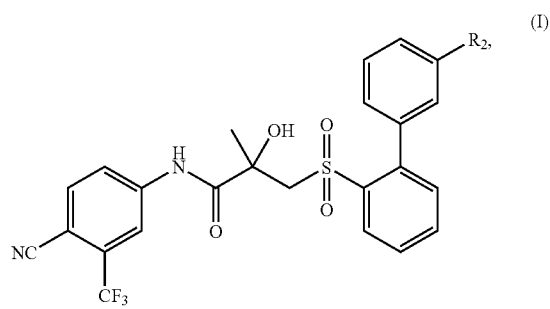

-continued

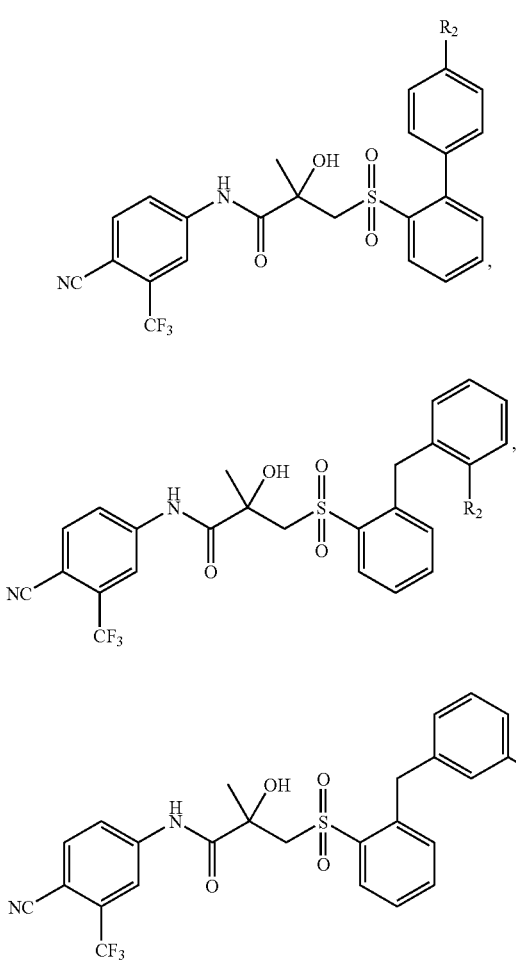

wherein R₂ is alkyl, alkoxy, aryl, branched alkyl, branched alkyloxy, alkylamino, dialkylamino, aryloxy, arylamino, acyl, alkylamido, or alkylcarbamoyl, provided that, when R₂ is alkyl or branched alkyl, the alkyl or branched alkyl is substituted with amino, alkylamino, dialkylamino, carboxyl, ester, hydroxy, alkoxy, sulfonyl or cyano; further provided that, when R₂ is alkoxy, aryl, branched alkyloxy, alkylamino, dialkylamino, aryloxy, arylamino, acyl, alkylamido, or alkylcarbamoyl is optionally substituted with alkyl, amino, alkylamino, dialkylamino, carboxyl, ester, hydroxy, alkoxy, sulfonyl or cyano.

3. The compound of claim 2, selected from the group consisting of:

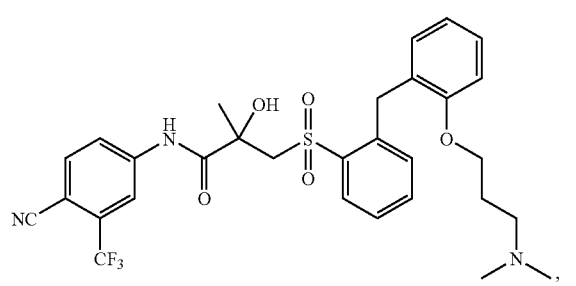

-continued

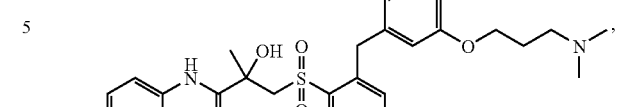

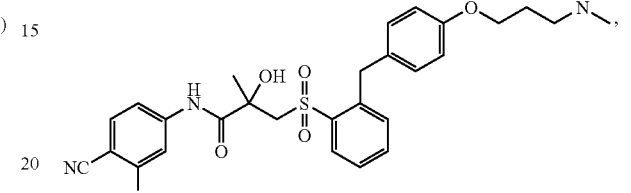

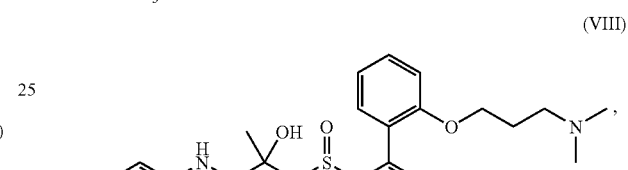

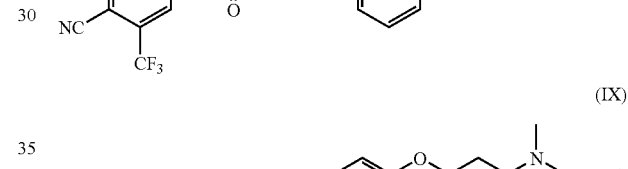

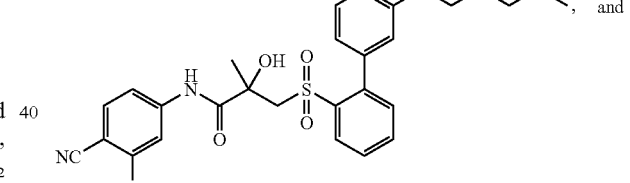

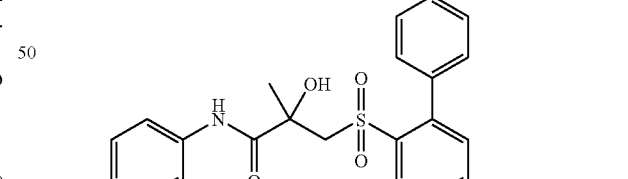

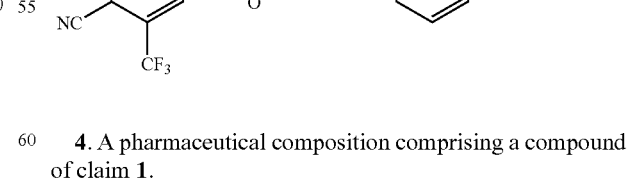

4. A pharmaceutical composition comprising a compound of claim 1.

* * * * *